US011331396B2

(12) United States Patent
Andresen et al.

(10) Patent No.: US 11,331,396 B2
(45) Date of Patent: May 17, 2022

(54) DEVELOPMENT OF INJECTABLE FIDUCIAL MARKERS FOR IMAGE GUIDED RADIOTHERAPY WITH DUAL MRI AND CT VISIBILITY

(71) Applicants: TECHNICAL UNIVERSITY OF DENMARK, KGS. Lyngby (DK); NANOVI RADIOTHERAPY APS, KGS. Lyngby (DK)

(72) Inventors: Thomas Andresen, Vanløse (DK); Rasmus Irming Jølck, Kgs. Lyngby (DK); Linda Maria Bruun, Kopenhagens (DK)

(73) Assignees: TECHNICAL UNIVERSITY OF DENMARK, Kgs. Lyngby (DK); NANOVI RADIOTHERAPY APS, Kgs. Lyngby (DK)

( * ) Notice: Subject to any disclaimer, the term of this patent is extended or adjusted under 35 U.S.C. 154(b) by 0 days.

(21) Appl. No.: 16/615,504

(22) PCT Filed: May 24, 2018

(86) PCT No.: PCT/EP2018/063657
§ 371 (c)(1),
(2) Date: Nov. 21, 2019

(87) PCT Pub. No.: WO2018/215595
PCT Pub. Date: Nov. 29, 2018

(65) Prior Publication Data
US 2020/0222560 A1    Jul. 16, 2020

(30) Foreign Application Priority Data

May 24, 2017   (SE) .................................. 1750654-4

(51) Int. Cl.
| | | |
|---|---|---|
| A61K 49/10 | (2006.01) | |
| A61K 49/08 | (2006.01) | |
| A61K 9/00 | (2006.01) | |
| A61K 47/26 | (2006.01) | |
| A61K 49/12 | (2006.01) | |

(52) U.S. Cl.
CPC .......... *A61K 49/108* (2013.01); *A61K 9/0019* (2013.01); *A61K 47/26* (2013.01); *A61K 49/085* (2013.01); *A61K 49/126* (2013.01)

(58) Field of Classification Search
CPC . A61K 9/00; A61K 9/06; A61K 47/26; A61K 49/10; A61K 49/08; A61K 49/12
See application file for complete search history.

(56) References Cited

U.S. PATENT DOCUMENTS 5,356,635 A * 10/1994 Raman ................. A61K 9/2013
424/423
2016/0089454 A1* 3/2016 Andresen ........... A61K 49/0457
424/1.11

FOREIGN PATENT DOCUMENTS

| | | |
|---|---|---|
| WO | 2014187962 | 11/2014 |
| WO | 2015/004669 | 1/2015 |
| WO | 2016/079331 | 5/2016 |
| WO | 2016/079332 | 5/2016 |
| WO | 2016079330 | 5/2016 |

OTHER PUBLICATIONS

International Search Report for PCT/EP2018/063657 dated Sep. 13, 2018, 3 pages.
L. Donaldson, Radiotherapy Risk Profile, Technical Manual, Geneva, Switzerland World Health Organization Press, Jan. 2008.
Rajamanickam Baskar et al., "Cancer and Radiation Therapy: Current Advances and Future Directions", International Journal of Medical Sciences, Feb. 2012.
Shikha Goyal et al., "Image Guidance in Radiation Therapy: Techniques and Applications", Radiology Research and Practice, Dec. 2014.
Michael J. Zelefsky, M.D., et al., "Improved Clinical Outcomes With High-Dose Image Guided Radiotherapy Compared With Non-IGRT for the Treatment of Clinically Localized Prostate Cancer", International Journal of Radiation Oncology, Nov. 2011.
C.F. Njeh, "Tumor delineation: The weakest link in the search for accuracy in radiotherapy", Journal of Medical Physics, Oct. 2008.
Antonio Luna et al., "Functional Imaging in Oncology", Biophysical Basis and Technical Approaches, Jul. 2014.
Zhanrong Gao et al., "A study of prostate delineation referenced against a gold standard created from the visible human data", Radiotherapy and Oncology, Nov. 2007.
Geert M. Villeirs et al., "Interobserver Delineation Variation Using CT versus Combined CT + MRI in Intensity-Modulated Radiotherapy for Prostate Cancer", Strahlentherapie und Onkologie, Apr. 2005.
Alexei Bogdanov Jr., et al., "Molecular MR Contrast Agents for the Detection of Cancer: Past and Present", Semin Oncol., Feb. 2011.
Joakim H. Jonsson et al., "Internal Fiducial Markers and Susceptibility Effects in MRI—Simulation and Measurement of Spatial Accuracy", Int. J. Radiation Oncology Biol. Phys., Apr. 2012.

(Continued)

*Primary Examiner* — Michael G. Hartley
*Assistant Examiner* — Jagadishwar R Samala
(74) *Attorney, Agent, or Firm* — Tutunjian & Bitetto, P.C.

(57) ABSTRACT

Radiation therapy or radiotherapy (RT) is a powerful treatment where precision and accuracy is crucial. Image Guided Radiotherapy (IGRT) facilitates more accurate position verification, correcting for anatomic changes related to internal organ movement. IGRT thereby helps reduce toxicity of radiotherapy and increases relapse-free survival. An inter-correlation point with a fixed position and volume (a marker) can be applied to indicate the point of treatment clearly in both imaging modalities and to localize and track tumors in real time. In this study, we present the development of a marker based on lactose octaacetate:octapropionate 1:1 containing 3 mM PLA-DTPA(Gd), 40% triglyceride, 5% propylene carbonate and 10% XSAIB (sucrose based CT-contrast agent). The injectable marker had high CT contrast (>1000 HU) and displayed clearly visible, stable $T_1$ contrast enhancement ($T_1$~900 ms) in the rim over at least 3 weeks with clinically observable resolution.

19 Claims, 12 Drawing Sheets

(56) References Cited

OTHER PUBLICATIONS

C.C. Parker et al., "Magnetic resonance imaging in the radiation treatment planning of localized prostate cancer using intra-prostatic fiducial markers for computed tomography co-registration", Radiotherapy and Oncology, Feb. 2003.
Clifton David Fuller, MD, et al., "Fiducial Markers in Image-guided Radiotherapy of the Prostate", US Oncological Disease, Jan. 2006.
Rasmus L. Jølck et al., "Injectable Colloidal Gold in a Sucrose Acetate Isobutyrate Gelating Matrix with Potential Use in Radiation Therapy", Advanced Healthcare Materials, Apr. 2014.
Jonas Scherman Rydhög et al., "Quantification and comparison of visibility and image artifacts of a new liquid fiducial market in a lung phantom for image-guided radiation therapy", The International Journal of Medical Physics Research and Practice, May 2015.
Alvin Szeto et al., "Image-guided radiation therapy using surgical clips for localization of colonic metastasis from thyroid cancer", Radiation Oncology, Dec. 2014.
Nanovi Website Text, BioXmark—The role of fiducial markers, Updated Aug. 2019.
Zhuxian Zhou et al., "Gadolinium-Based Contrast Agents for MR Cancer Imaging", Wiley Interdiscip Rev Nanomed Nanobiotechnol, Jan. 2013.
Nazila Kamaly et al., "Chemistry of Tumour Targeted T1 Based MRI Contrast Agents", Current Topics in Medicinal Chemistry, Nov. 2010.
Thomas Courant et al., "Hydrogels Incorporating GdDOTA: Towards Highly Efficient Dual T1/T2 MRI Contrast Agents", Angewandte Chemie International Edition, Aug. 2012.
Minnie Chan, "Long-Lasting and Efficient Tumor Imaging Using a High Relaxivity Polysaccharide Nanogel Magnetic Resonance Imaging Contrast Agent", Biomacromolecules, Aug. 2015.
Stephane Dumas et al., "High relaxivity MRI contrast agents part 1: Impact of single donor atom substitution on relaxivity of serum albumin-bound gadolinium complexes", Invest Radiol, Oct. 2010.
Karl-Heinz Herrmann et al., "Possibilities and limitations for high resolution small animal MRI on a clinical whole-body 3T scanner", Magn Reson Mater Phy, Sep. 2011.
Swedish Search Report for Patent Application No. 1750654-4 dated Dec. 21, 2017 (3 pages).

* cited by examiner

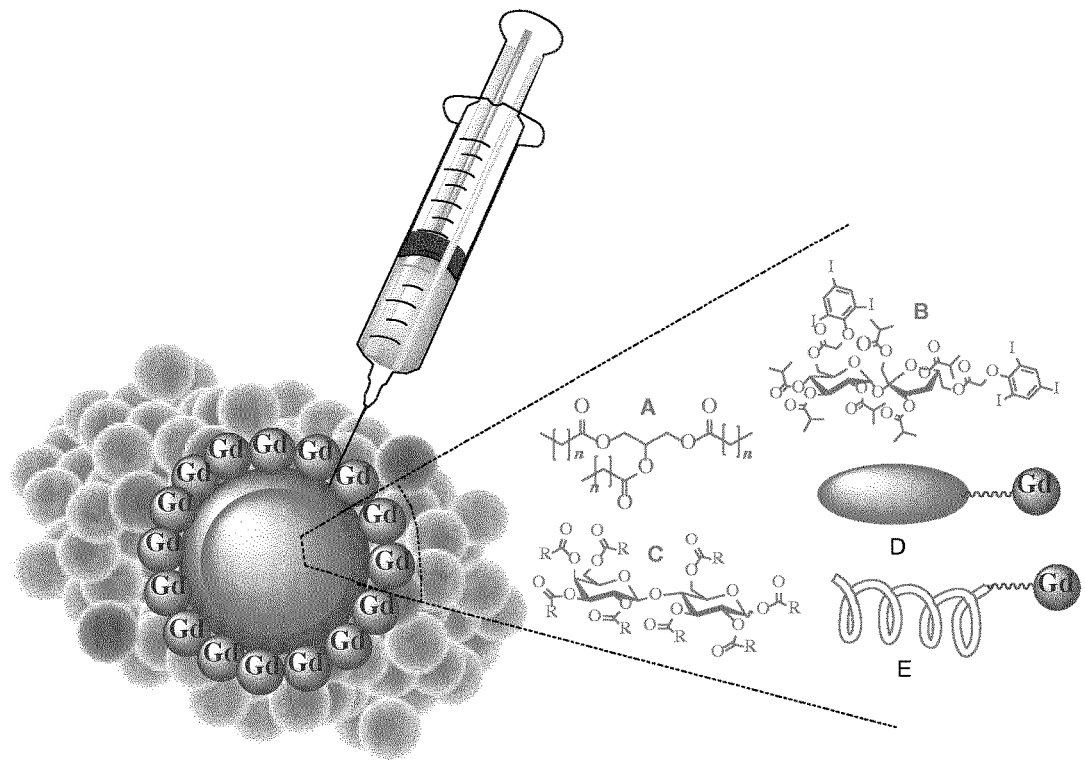

*Figure 1.* Schematic of the injectable dual CT/MRI fiducial marker after injection into tumor tissue. The material is based on lactose ester (C) and short chain triglycerides (A), CT contrast (B, XSAIB) and amphiphilic Gd-chelating molecules (D or E). While the CT contrast agent distributes itself quite evenly within the carbohydrate-triglyceride matrix (indicated by pink) due to its primarily hydrophobic nature, MRI contrast ($T_1$ contrast) comes from Gd-chelating amphiphiles (amphiphilic lipids (D): here DOPE/BSA or polymers (E): here PLA functionalized with a Gd chelator (DOTA or DTPA)) capable of diffusing to the rim of the injected material and affect $T_1$ of the surrounding water molecules in the tumor, resulting in a bright rim (indicated by purple) around the injected material.

LAP/LI + 40% TG and 5% PC/10% EtOH, LI + 40% GTO + DOPE-RhB a)

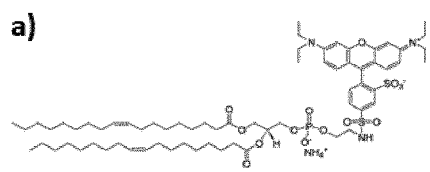

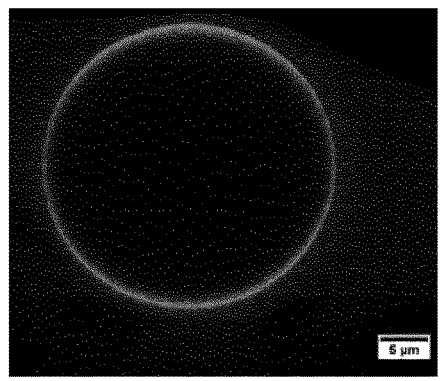

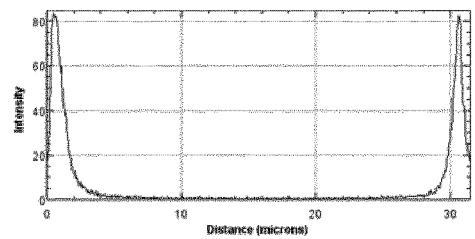

LAP/LI + 40% TG and 5% PC/10% EtOH, LI + 40% GTO + DOPE-CF b)

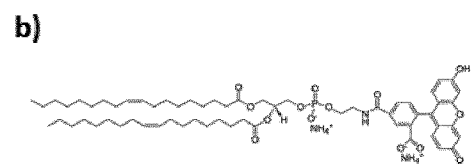

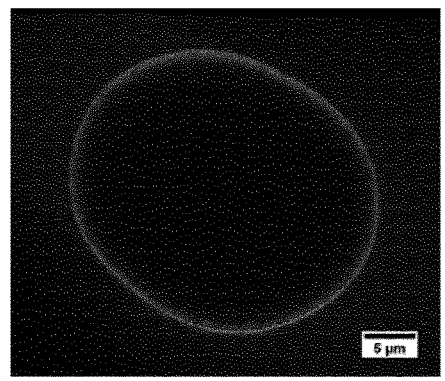

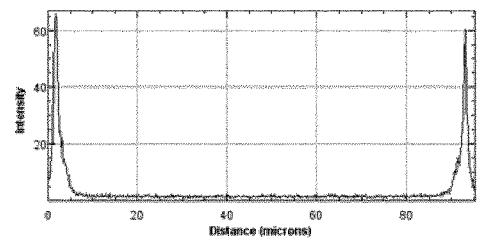

*Figure 2*: Confocal microscopy images and line profiles of best performing lactose octaacetate:lactose octapropionate 1:1 (LAP) and Lactose octaisobutyrate (LI) formulations in PBS co-formulated with DOPE-RhB (a) or DOPE-CF (b). As all the best formulations gave largely the same results in terms of line profile and confocal image. A representative formulation (LAP, 40% GTH, 5% PC) is shown in the figure for both lipids.

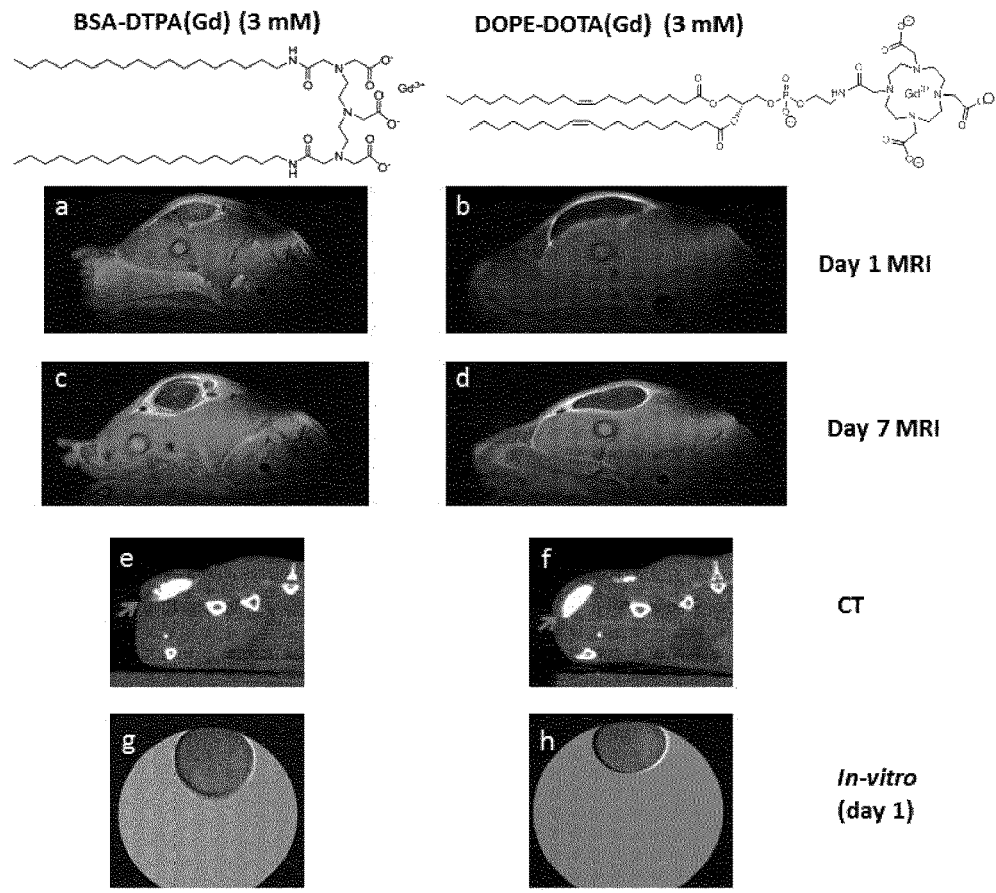
Figure 3. In-vitro (in PBS) (g-h) and In-vivo (subcutaneous injection) (a-f) imaging (T1 RARE) of formulations consisting of LAP 1:1, 40% GTH and 5% PC with ~3 mM of Gd-chelating lipid. The red arrows show the location of the injected materials on the CT images (e,f).

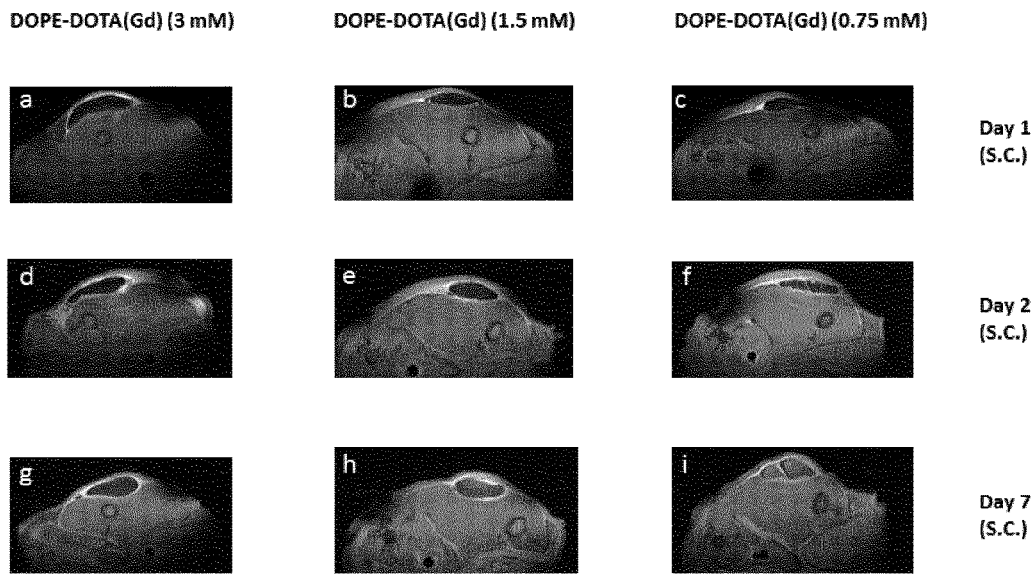

Figure 4. In-vivo imaging (T1 RARE) of different concentrations of DOPE-DOTA (Gd) imaged at day 1 (a-c), day 2 (d-f) and day 7 (g-i) after injection. Concentrations lower than 0.75 mM did not produce significantly different contrast from the rim of formulations without contrast agent, and are therefore not displayed in the figure (see supporting information for $T_1$ values of these materials). The 3 mM concentration clearly gave the best $T_1$ enhancement. All formulations display leakage of Gd-chelating lipid to the subcutaneous compartment (a white streak right under the skin in the area close to the injected materials.

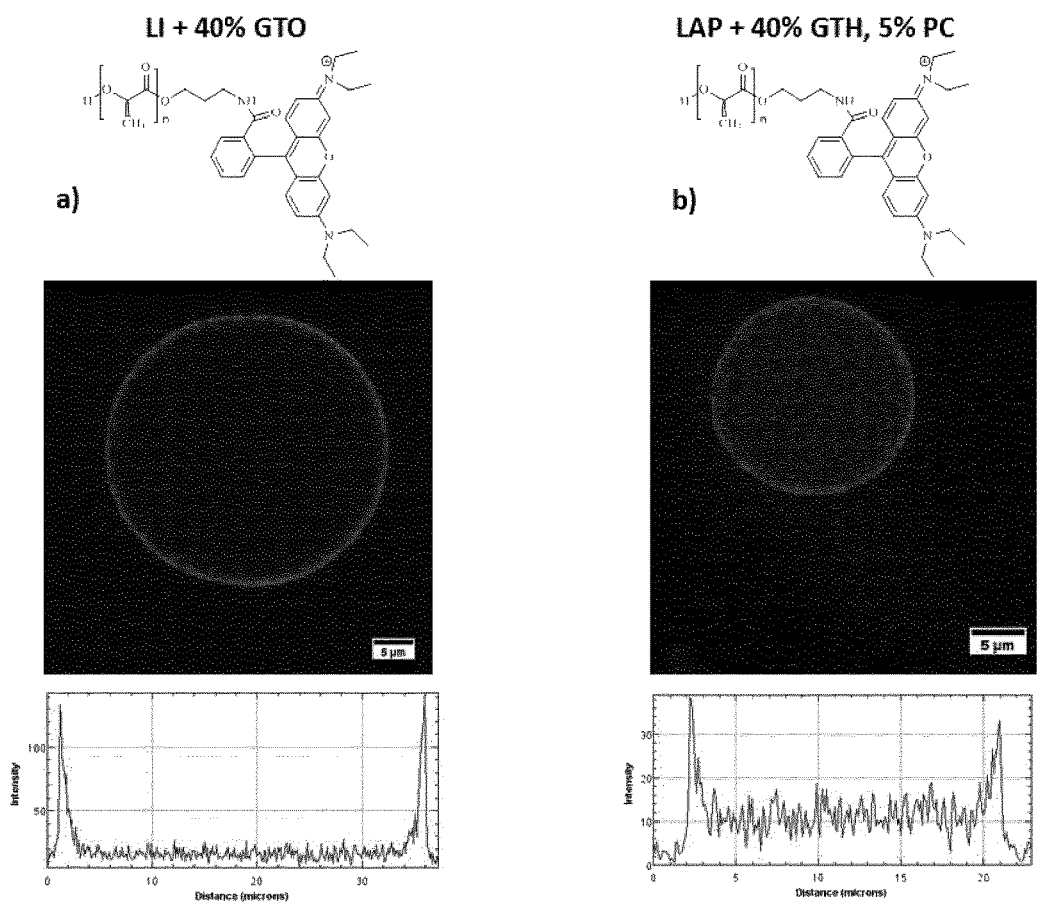
*Figure 5*: Confocal microscopy images and line profiles of lactose octaacetate:lactose octapropionate 1:1 (LAP) (a) and Lactose octaisobutyrate (LI) (b) formulations co-formulated with PLA-RhB (Mn ~3000).

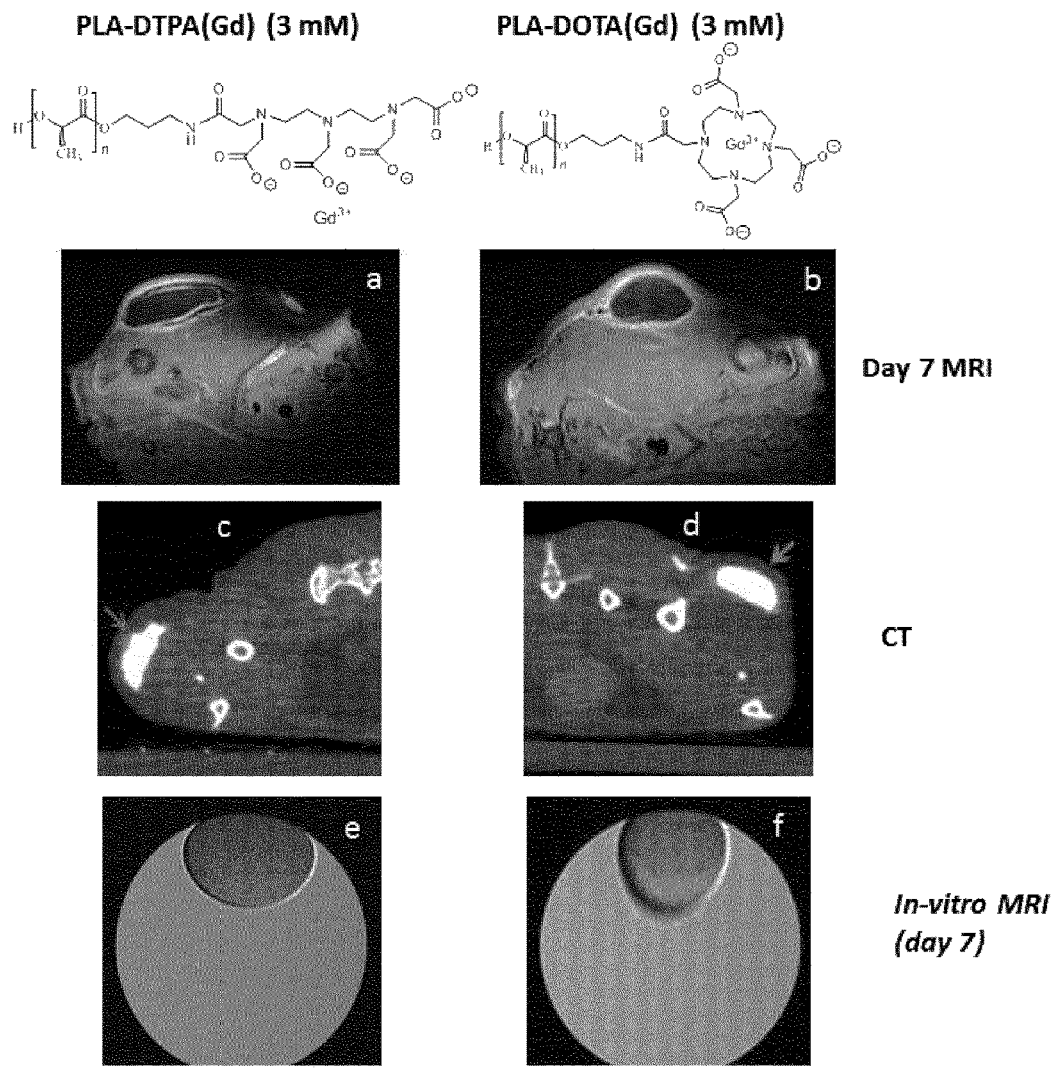
*Figure 6.* In-vitro (in PBS) (e-f) and In-vivo (subcutaneous injection) (a-d) imaging (T1 RARE) of materials formulated with ~3 mM of Gd-chelating PLA polymer (LAP 1:1, 40% GTH and 5% PC formulation). The (red) arrows show the location of the materials on CT scans (c, d).

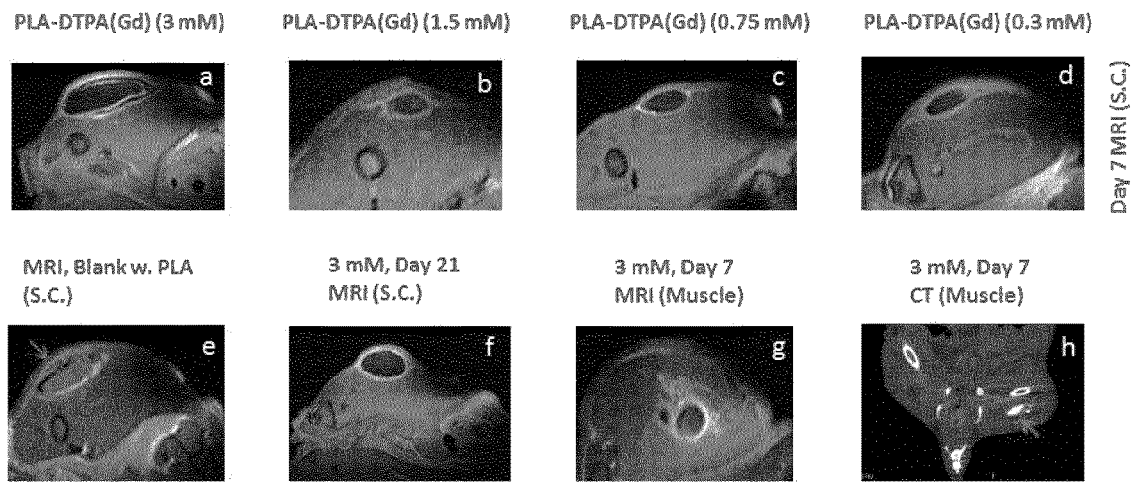

*Figure 7.* Further in-vivo studies of the PLA-DTPA(Gd) formulations in different concentrations upon s.c. injection (a-d) compared with the blank (e), the highest concentration 3 weeks after injection (s.c.) (f), and the highest concentration injected in a leg muscle (MRI (g) + CT (h)). The (red) arrows shows the location of the injected material on the CT image (h) and on the MRI image of the blank (e).

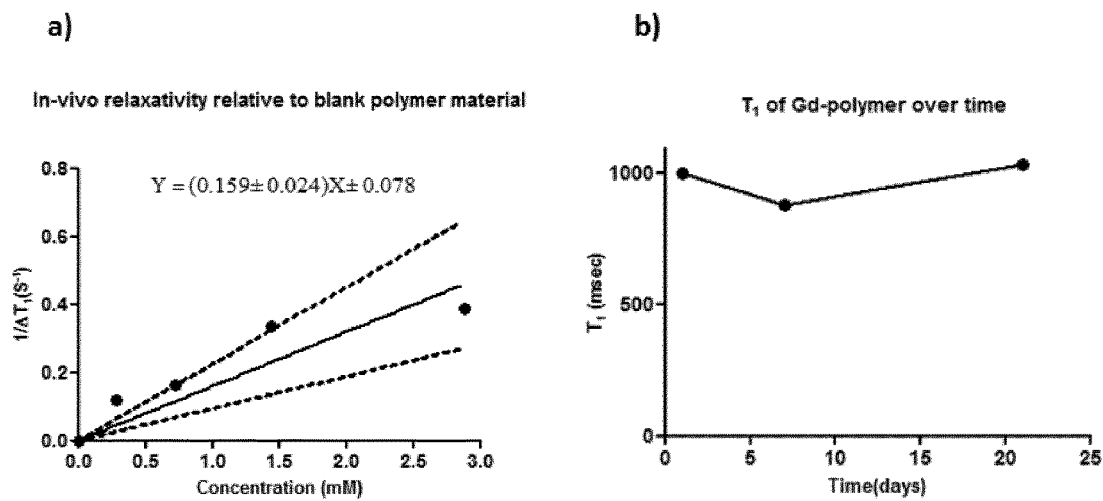

*Figure 8.* In-vivo relaxativity plot of the PLA-DTPA(Gd) formulations imaged in Figure 7 (a) as well as T1 contrast level in-vivo over time of the 3 mM formulation (b). Due to the pilot-nature of this study (only 1 mouse/ formulation), the measured relaxativity is not an absolute but rather an approximate value, made clear by the standard errors of the slope as well as the intercept shown in the curve equation ($r^2 \sim 0.76$). The T1 contrast stayed at a relatively stable level throughout the 3-week period.

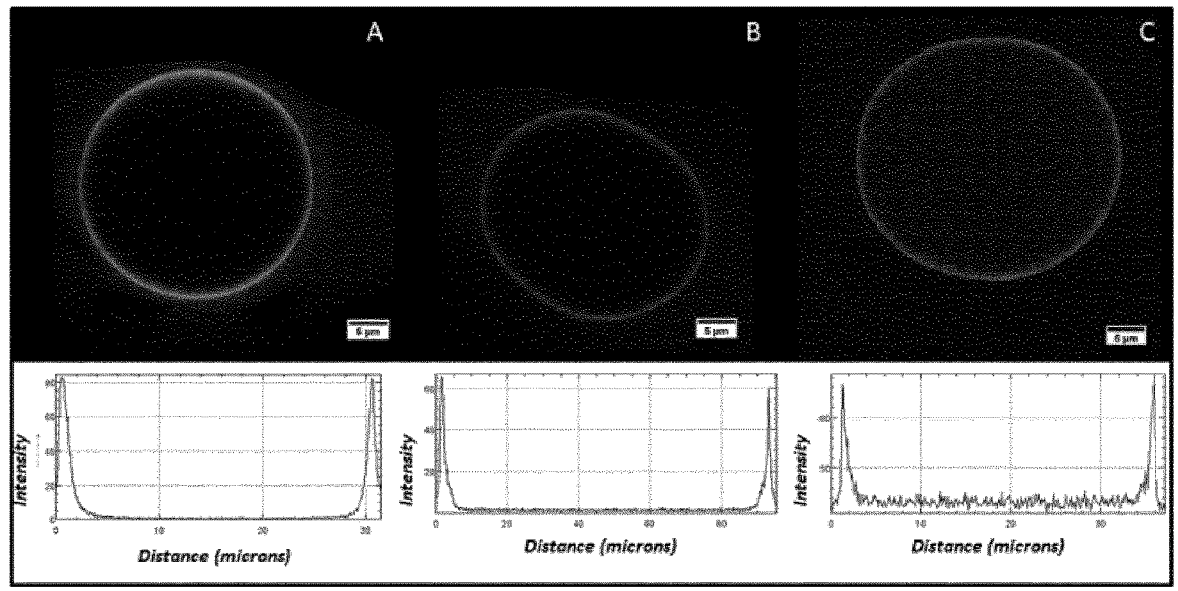
*Figure 9.* Confocal images and line profiles of formulation 5 (A), 8 (B) and 3 (C) from Table 1. All formulations in Table 1 show clear predominant accumulation at the marker rim, like the examples in this figure.
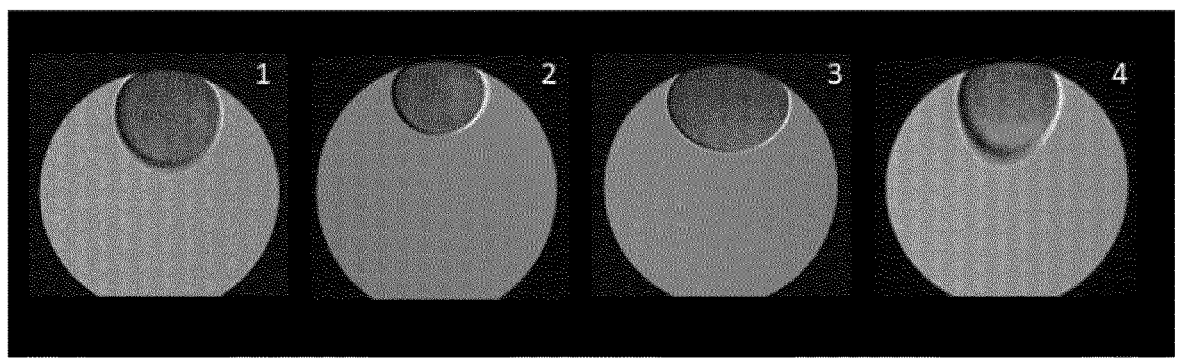
*Figure 10.* T1 RARE imaging of 50 µL markers of formulation 1-4 in designated order. All markers display a bright $T_1$ contrast enhancement at the rim in PBS buffer.

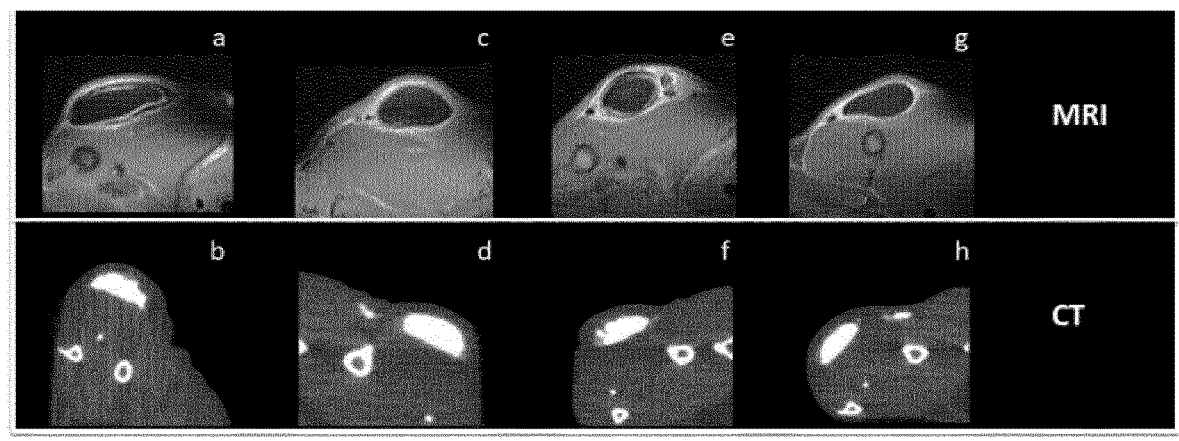

*Figure 11.* In-vivo MRI (T1 RARE) and CT imaging of subcutaneous markers formed from formulation 3 (a-b), 4 (c-d), 1 (e-f) and 2 (g-h) in Table 2, all imaged 7 days post injection. The lipid Gd-chelators result in $T_1$ enhancement of the subcutaneous compartment, indicating leakage of lipid-chelators over time. The markers containing PLA-DTPA(Gd) or PLA-DOTA(Gd), do not show clear signs of leakage in the images, and formulation 3 (a-b) shows clear $T_1$ enhancement still localized to the rim of the marker a week after injection ($T_1$ ~877 ms).

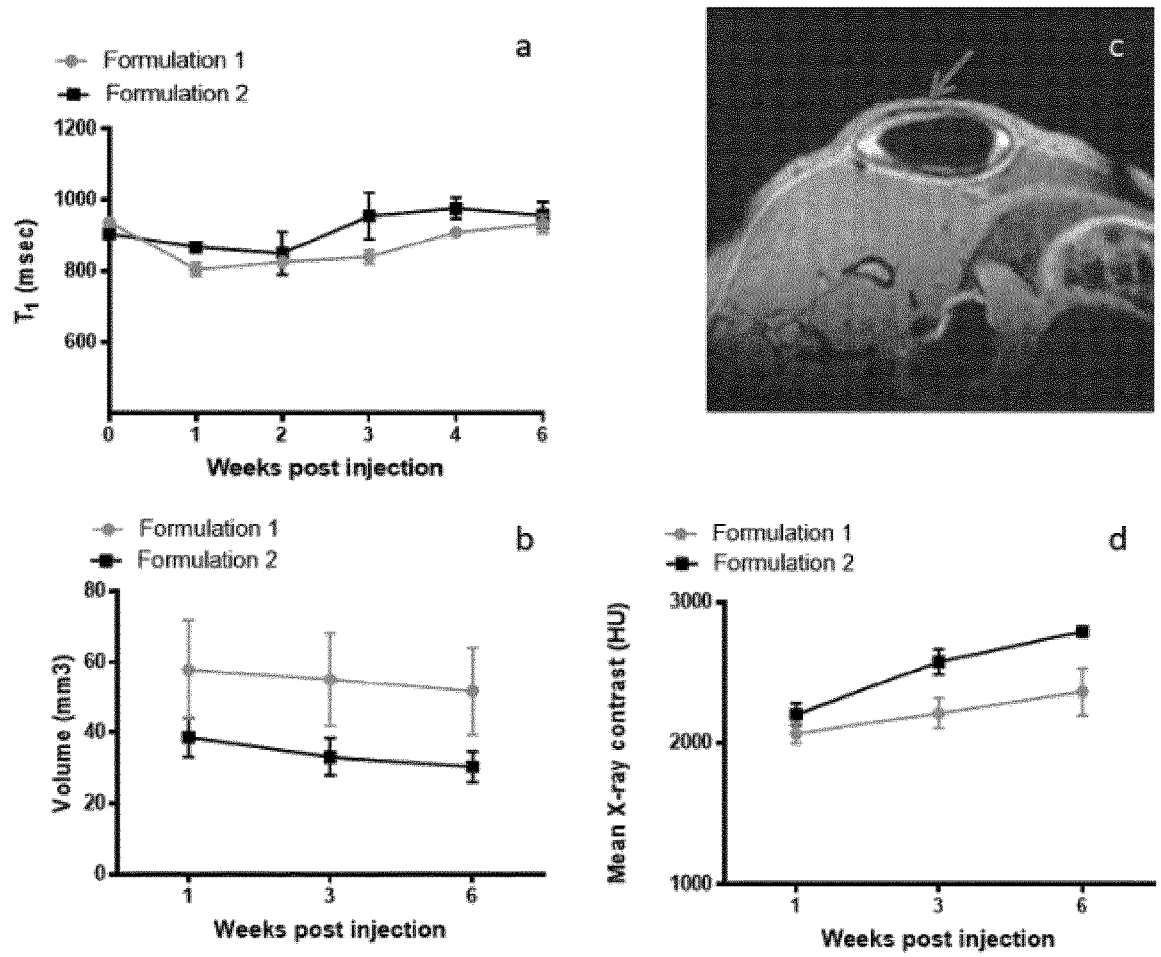

*Figure 12.1.* $T_1$ *contrast enhancement (a), Volume (b) and mean X-ray contrast (c) monitored over time after subcutaneous injection of formulation 1+2,* Table 4 *(N=4, Mean ± SEM). Both formulations display clear CT contrast of the resulting markers as well as $T_1$ contrast enhancement at the marker rim, a typical example is seen in image image 12.1 c (marker indicated by red arrow). Marker volumes of both formulations remain fairly stable over time.*

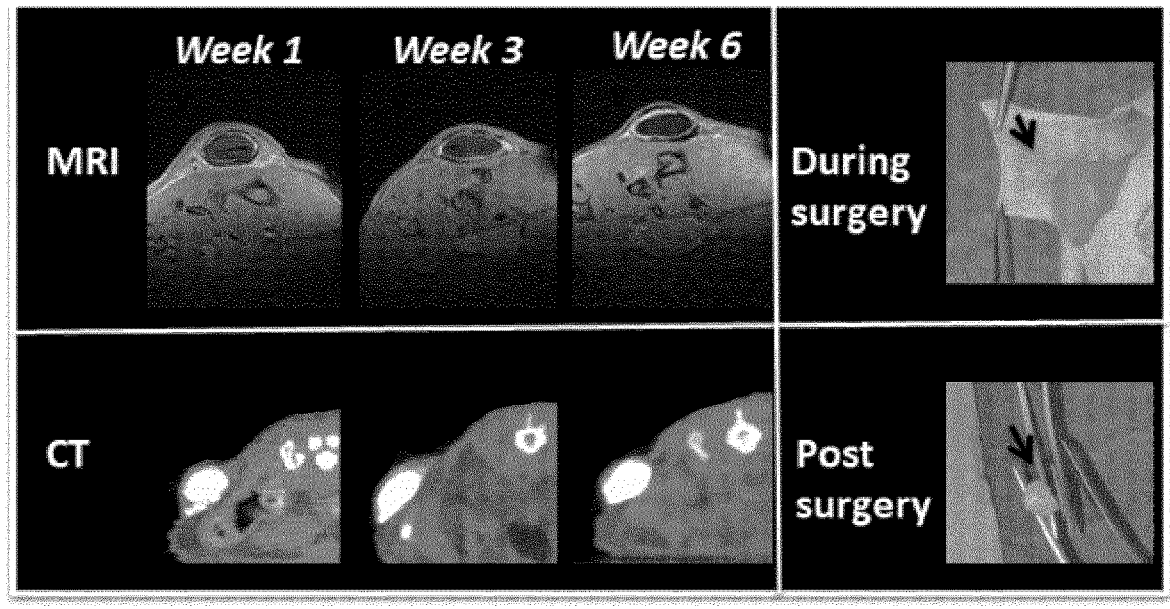

*Figure 12.2.* MRI and CT scan images of formulation 1, Table 4 markers. Both formulation 1 and 2, Table 4, result in markers with clear $T_1$ contrast enhancement at the water-marker interface. The right side of the figure shows a marker (formulation 2, Table 4) during and after surgical removal (marker indicated by black arrow). The marker was fully intact and easy to remove, no irritation or inflammation of the surrounding tissue was observed.

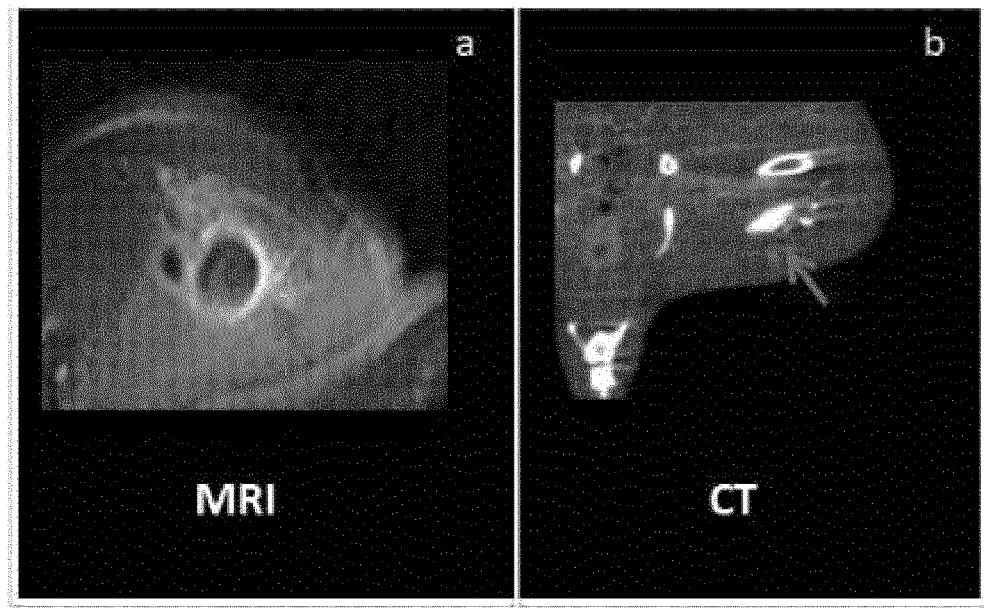

*Figure 13.* MRI imaging (a) and CT imaging (b) of the intramuscular marker 7 days post injection (marker is indicated by red arrows). As seen on image a), there is clear $T_1$ contrast enhancement at the rim. From both CT and MRI imaging, slight marker fragmentation is seen due to the moving muscle tissue, however the majority of the marker remains localized at the place of injection.

DEVELOPMENT OF INJECTABLE FIDUCIAL MARKERS FOR IMAGE GUIDED RADIOTHERAPY WITH DUAL MRI AND CT VISIBILITY

INTRODUCTION

Radiation therapy or radiotherapy (RT) is an important therapy form used in combination with surgery and chemotherapy for the treatment of cancer [1]. Radiotherapy relies on the use of ionizing radiation, and is therefore very dependent on precision and accuracy. Therefore, increasing emphasis is being laid on optimizing radiotherapy volume while facilitating tumor targeted delivery of high radiotherapy doses, resulting in a more efficient treatment with reduced risk of radiation damage to adjacent normal tissues [2]. Image Guided Radiotherapy (IGRT). IGRT facilitates more accurate position verification during the course of fractionated radiotherapy in order to correct for change in tumor position related to internal organ movement caused by respiration, peristalsis and rectal/bladder filling [3]. Thereby IGRT helps reduce toxicity of radiation treatment while leading to a higher fraction of relapse-free survival [4].

The most frequently used imaging-technique for IGRT is Computed Tomography (CT) due to its ability to visualize tumors in both a time- and cost-effective manner. However, CT-based target delineation of soft tissue tumors tends to only improve the precision and not the accuracy of tumor delineation for radiotherapy treatment. An important reason for this is the relatively low soft tissue resolution of this imaging technique [5, 6]. An example of this was seen by Gao et al [7], by comparing prostate delineations on CT with anatomical photos, an overestimated target volume of ~30% was observed on CT, comparable to the differences in target delineation between CT and MRI. For example, on average, ~40% larger prostate volumes are defined on CT compared to MRI, a technique with submillimeter soft tissue resolution [7, 8, 9]. CT-delineations of the prostate also tends to underestimate the dimensions in the posterior direction, here MRI has a clearly more accurate visualization of prostate anatomy [7, 10, 11]. These observations clearly indicate that it is advantageous to apply both CT and MRI in planning of soft tissue tumor radiotherapy in order to obtain images with sufficient resolution and accurate dimensions. An inter-correlation point with a fixed position and volume (a marker) can be applied to guide treatment planning on both CT and MRI imaging. Such a marker would allow for an easy correlation between the two imaging modalities and a fixpoint to track moving soft tissue tumors on CT in real time during treatment [10].

Fiducial markers are used in IGRT in order to track soft tissue tumors in moving tissues where the actual position cannot clearly be correlated to bony anatomy, which is the case for most tumors in abdominal organs and in the lungs [12, 13]. Injectable, fiducial markers based on SAIB (Sucrose Acetate Isobutyrate), ethanol and gold-nanoparticles or a iodine-rich sucrose esters (XSAIB) have been developed in order to improve a technology formerly dominated by solid, difficult to administer markers such as gold seeds [13,14]). The novel SAIB-based fiducial markers are easily administered, non-toxic, biodegradable markers with high CT contrast and high stability over the entire course of radiotherapy [3, 15]. While SAIB-based markers are readily visible in the CT modality due to the high content of heavy atoms (Au or I), the markers result in a hypointense signal in $T_1$-weighted MRI, often difficult to visualize in tumor tissue [16]. In order to facilitate better visualization in the MRI modality, a Gd chelating moiety can be incorporated in the fiducial marker formulations, resulting in a positive (bright) $T_1$ contrast, easily visualized in the tumor area [17]. Gd-complexes provide high $T_1$ contrast enhancement and are highly stable. They work by shortening of the $T_1$ relaxation of surrounding water molecules.

Gd chelating injectable gels and gel-like formulations are known from literature as a means of achieving high local $T_1$ contrast due to stable, slow tumbling, poly-functionalized complexes often constructed from polymeric materials [18]. The systems described in literature mainly consist of hydrophilic polysaccharides such as chitosan and hyaluronan functionalized with Gd chelators [19, 20] displaying high $T_1$ contrast and retention in tumors lasting several days, however these hydrophilic systems are often not injectable in sufficiently high concentrations, therefore nanoparticle formulations are constructed, and clearance of such particles is relatively fast (within days) from the tumor area, requiring repeated administration. Formulations injectable through thin needles in long endo- or bronchoscopes (EUS/EBUS) and capable of retaining the same size and shape over the typical 6-week period of a fractionated radiotherapy regime, represent the most optimal design. Therefore, the design described in this article is based on injectable, non-viscous formulations of different lactose esters (octaacetate:octapropionate 1:1 or octaisobutyrate) co-formulated with low percentage of solvent and/or short chain triglycerides. The hydrophobicity of the formulations can be tuned to fit the loaded contrast agents as well as therapeutic molecules such as radiosensitizers or other therapeutic molecules loaded in the material to potentiate the effect of radiotherapy. The formulations contain 10 wt % XSAIB (6,6'-di-triiodobenzene-isobuturic-sucrose,) as CT contrast agent and amphiphilic or hydrophilic Gd-chelating molecules (lipids or polymers) as MRI contrast agent. While the hydrophobic CT contrast agent is relatively uniformly distributed throughout the whole formulation, the amphiphilic or hydrophilic Gd-chelating constructs are capable of diffusing to the rim of the material upon injection, providing contrast enhancement at the rim (FIG. 1). The presented design provides a clear distinction between CT contrast and MRI contrast in the marker. The work presented in this article provides promising initial results, indicating a clinically applicable concept under development.

SUMMARY OF THE INVENTION

The present invention is directed to a composition for at least MR imaging, comprising non-water soluble carbohydrates, wherein at least 50% of the non-water soluble carbohydrates are carbohydrates selected from derivatives of lactose, maltose, trehalose, raffinose, glucosamine, galactosamine, lactosamine, sucrose or derivatives of sucrose, or mixed saccharides, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament, wherein the composition contains at least one imaging contrast agent, and wherein the composition provides a phase separation which provides a clear contrast distinction in MR imaging.

To relate further to prior art, WO2014/187962 discloses an X-ray contrast composition for local administration, wherein the X-ray contrast composition exhibits contrast properties and wherein at least 60% of an administrated amount of said X-ray contrast composition remains more than 24 hours within 10 cm from an injection point when the X-ray contrast composition is administrated to a human or animal body.

Moreover, in WO2016/079330 there is disclosed a composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament.

None of the documents above relate to a composition providing a phase separation such as the composition according to the present invention. The phase separation provided according to the present invention enables the provision of a clear contrast distinction in MR imaging, and especially when MR imaging and CT is combined. This is not hinted or disclosed in WO2014/187962 or WO2016/079330.

BRIEF DESCRIPTION OF THE DRAWINGS

FIG. 1 is a schematic of injectable dual CT/MRI fiducial marker after injection into tumor tissue;

FIG. 2 depicts microscopy images and line profiles of lactose oclaacetate;lactose octapropionate 1:1 (LAP) and Lactose octaisobutyrate (LI) formulations;

FIG. 3 depicts in-vitro and in-vivo imaging of LAP 1:1, 40% GTH and 5% PC with ~3 mM of Gd-chelating lipid formulations;

FIG. 4 depicts in-vivo imaging of different concentrations of DOPE-DOTA (Gd) imaged at day 1, day 2 and day 7 after injection;

FIG. 5 depicts microscopy images and line profiles of lactose octaacetate;lactose octapropionate 1:1 (LAP) and lactose octaisobutyrate (LI) formulations coformulated with PLA-RhB;

FIG. 6 depicts in-vitro and in-vivo imaging of materials formulated with ~3 mM of Gd; chelating PLA polymer;

FIG. 7 depicts further in-vivo studies of the PLA-DTPA (Gd) formulations in different concentrations upon injection;

FIG. 8 depicts in-vivo relaxativity plot of the PLA-DTPA (Gd) formulations imaged in FIG. 7 and T1 contrast level in-vivo over time of the 3 mM formulation;

FIG. 9 depicts confocal images and line profiles of formulation 5 from Table 1;

FIG. 10 depicts T1 RARE imaging of 50 µL markers of formulation 1-4 in designated order;

FIG. 11 depicts in-vivo MRI and CT imaging of subcutaneous markers formed from formulation 3, 4, 1 and 2;

FIG. 12.1 depicts contrast enhancement, volume and mean X-ray contrast monitored over time after subcutaneous injection of formulation 1+2;

FIG. 12.2 depicts MRI and CT scan images of formulation 1, Table 4 markers; and

FIG. 13 depicts MRI imaging and CT scan imaging of the intramuscular marker 7 days post injection.

Experimental Procedures
Organic Synthesis
General Experimental Conditions:

All reactions were carried out under inert atmosphere ($N_2$). Water sensitive liquids and solutions were transferred via syringe. Water used for washing of the syntheses was in all cases pure MiliQ water. Organic solutions were concentrated by rotary evaporation at 30-60° C. under 200-0 milibar. Thin layer chromatography (TLC) was carried out using aluminium sheets pre-coated with silica 60F (Merck 5554). The TLC plates were inspected under UV light or developed using a cerium ammonium sulphate solution (1% cerium(IV)sulphate and 2.5% hexa-ammonium molybdate in a 10% sulfuric acid solution).

Reagents:

DOTA-NHS was purchased from Macrocyclics. All other chemicals were purchased from Sigma Aldrich and were used as received. Dry pyridine was obtained by drying over sieves (4 Å) for 2-3 days prior to use.

Instrumentation:

Nuclear Magnetic Resonance (NMR) was conducted on a Bruker Ascend™ 400 MHz—operating at 401.3 MHz for $^1H$ and 100.62 MHz for $^{13}C$—with a 5 mm H—Broadband Dual Channel z-gradient Prodigy cryoprobe at 298 K, using the residual solvent as internal standard. Recorded chemical shifts were reported in parts per million (δ=scale) downfield from tetramethylsilane, and all coupling constants (J) are expressed in Hz. The FID files were processed in Mnova Suite version 8.1.4. In $^1H$-NMR spectra of α,β anomeric mixtures, the integral of H-1 of the most abundant anomer was always set to 1.0, and the percentage of each anomeric species was calculated from the integral ratio of H-1 α and H-1 β. MALDI-TOF MS was conducted on a Bruker Autoflex Speed™ instrument. The matrix used for MALDI-TOF was a mixture of 2,5 dihydroxy benzoic acid (DHB), trifluoroacetic acid and $Na^+$ in ethanol. Preparatory HPLC was conducted on a Waters 600 pump and controller with a Waters 2489 UV/Vis detector.

General Experimental Procedure for Synthesis of Lactose Esters

β-lactose (typically 10-100 g) was suspended in dry pyridine under inert atmosphere ($N_2$). Hereafter, acetic, propionic or isobutyric anhydride (~2.2 eq pr OH) was carefully added, followed by a catalytic amount of DMAP (~0.1 eq). The reactions were heated to ~48° C. overnight and then continued for ~24 H at r.t. The reactions were then concentrated in vacuuo and co-evaporated with toluene. The concentrates were dissolved in $CHCl_3$ and washed with $NaHCO_3$(aq) (3×), water (2×), and brine (1×). The organic phases were dried with $MgSO_4$ (s), filtered, concentrated under reduced pressure and dried in vacuuo. α,β lactose octaacetate. Yield: 93.7% yield (mixture of anomers: ~30% α and ~70% β). $^1H$-NMR: (400 MHz, Chloroform-d) δ 6.24 (d, J=3.7 Hz, 0.4H, H-1 α), 5.66 (d, J=8.3 Hz, 1H, H-1 β), 5.44 (dd, 10.28, 9.53 Hz, 0.4H), 5.37-5.31 (m, 2H), 5.23 (t, J=9.1 Hz, 1H), 5.15-5.00 (m, 3H), 4.99-4.91 (m, 2H), 4.50-4.41 (m, 3H), 4.17-4.05 (m, 4H), 3.99 (ddd, J=10.2, 4.3, 2.1 Hz, 0.4H, H5 α), 3.91-3.78 (m, 3H), 3.75 (ddd, J=9.9, 4.8, 2.0 Hz, 1H, H5 β), 2.19-1.93 (singlets, ~32H, $CH_3$ acetyls). MALDI TOF-MS: Calc $[M+Na]^+$: 701.59. Found: 701.51. α,β lactose octapropionate. Yield: 84% (mixture of anomers: ~30% α and ~70% β). $^1H$-NMR (400 MHz, Chloroform-d) δ 6.26 (d, J=3.7 Hz, 0.4H, H1-α), 5.68 (d, J=8.3 Hz, 1H, H-1 β), 5.47 (dd, 10.3, 9.2 Hz, 0.4H), 5.38-5.33 (m, 2H), 5.26 (t, J=9.2 Hz, 1H), 5.15-5.00 (m, 3H), 5.02-4.91 (m, 2H), 4.49-4.41 (m, 3H), 4.15-4.03 (m, 4H), 3.98 (ddd, J=10.1, 3.9, 1.8 Hz, 0.4H, H5 α), 3.91-3.77 (m, 3H), 3.73 (ddd, J=9.9, 4.6, 2.0 Hz, 1H, H5 β), 2.47-2.15 (m, ~23H), 1.19-0.99 (m, ~34H). MALDI TOF-MS: Calc $[M+Na]^+$: 813.80. Found: 813.42. α,β lactose octaisobutyrate. Yield: 89.5% (mixture of anomers: ~30% α and ~70% β). $^1H$ NMR (400 MHz, Chloroform-d) δ 6.26 (d, J=3.8 Hz, 0.4H, H-1α), 5.68 (d, J=8.3 Hz, 1H, H-1β), 5.48

(dd, J=10.3, 9.3 Hz, 0.4H), 5.40-5.34 (m, 2H), 5.27 (t, J=9.5 Hz, 1H), 5.18-5.00 (m, 3H), 5.03-4.91 (m, 2H), 4.50-4.41 (m, 3H), 4.24-4.02 (m, ~4H), 3.95 (ddd, J=10.1, 3.8, 1.7 Hz, 0.4H, H5 α), 3.91-3.80 (m, 3H), 3.70 (ddd, J=9.9, 4.5, 2.0 Hz, 1H, H5 β), 2.70-2.32 (m, ~11H), 1.26-1.01 (m, ~68H). MALDI TOF-MS: Calc [M+Na]$^+$: 926.02. Found: 925.70.

PLA-RhB. PLA-NH$_2$ (Mn~2500) (260 mg, 0.1 mmol) was suspended in dry DCM (~5 mL). Then, a pre-mixed mixture of Rhodamine-B (105, 0.2 mmol), EDC-HCl (80 mg, 0.4 mmol) and DMAP (106 mg, 0.9 mmol) dissolved in 5 mL dry DCM was added, and the reaction was continued at r.t. for ~2 days, where after Kaiser test (negative) indicated completion. The solvents were removed in vacuuo, and the crude mixture was dissolved in DMSO and purified by dialysis (Mw cutoff: 1000 da) against MQ water for ~14 days. Yield: 299 mg (97%). $^1$H NMR (400 MHz, DMSO-d$_6$) δ 8.31 (d (br), J=7.7 Hz, 1H), 7.95 (br. t, J=7.4 Hz, 1H), 7.87 (br. t, J=7.6 Hz, 1H), 7.57-7.44 (m, 2H), 7.05-7.00 (m, 1H), 6.39-6.24 (m, ~5H), 5.20 (q, J=7.1 Hz, ~33H), 3.65 (dd (br), J=13.8, 6.9 Hz, 4H), 3.31 (br. q, J=7.1 Hz, 8H), 3.12-2.94 (m, 2H), 1.47 (d, J=7.1 Hz, ~99H), 1.08 (t, J=6.9 Hz, 12H).

PLA-DTPA. PLA-NH$_2$ (Mn~2500) (260 mg, 0.1 mmol) was suspended in dry pyridine (~10 mL) followed by addition of DTPA-dianhydride (57.5 mg, 0.16 mmol) followed by a catalytic amount of DMAP (1.3 mg, 0.01 mmol). The reaction was continued for ~1.5 day, where after Kaiser test (negative) indicated that the reaction was completed. ~5 mL MQ water was added and stirred for ~2 h to hydrolyze the anhydride. The solvents were removed in vacuuo, and the crude mixture was dissolved in DMSO and purified by dialysis (Mw cutoff: 1000 da) against MQ water for ~8-10 days. Yield: 285 mg (96%). $^1$H NMR (400 MHz, DMSO-d$_6$) δ PLA-DTPA, DMSO-D6: 8.09 (s, NH, ~1H), 5.20 (q, J=7.0 Hz, ~33H), 4.21 (dd, J=6.0 Hz, 12.0 Hz, 2H), 4.17-4.01 (m, 4H), 3.45 (s, 2H), 3.38 (s, 2H), 3.26 (s, 2H), 3.14 (dd, J=12 Hz, 6.0 Hz, 2H), 2.99 (s, 2H), 2.86 (s, 2H), 2.70-2.64 (m, 2H), 2.35-2.29 (m, 2H), 1.74 (p, J=7.0 Hz, 2H), 1.47 (d, J=7.1 Hz, ~99H).

PLA-DOTA. PLA-NH$_2$ (Mn~2500) (80 mg, 0.032 mmol) was suspended in dry dichloromethane (~3 mL), followed by addition of DOTA-NHS (35 mg, 0.0704 mmol) and triethyl amine (40 µL). The reaction was continued for ~2.5 days at r.t., where after Kaiser test (negative) indicated completion. The solvent was removed in vacuuo, and the crude mixture was dissolved in DMSO and purified by dialysis (Mw cutoff: 1000 da) against MQ water for ~8-10 days. Yield: 89.6 mg (~97%). $^1$H NMR (400 MHz, DMSO-d$_6$) δ 8.23 (s, NH, ~1H), 5.21 (q, J=7.0 Hz, ~33H), 4.21 (dd, J=13.6, 6.8 Hz, 2H), 4.09 (2×dd, J=13.6, 6.8, 2H), 3.42 (d of s, ~6H), 3.22-3.03 (m, ~6H), 3.03-2.87 (m, ~10H), 2.65 (d of s, 2H), 1.79 (p, J=6.9 Hz, 2H). 1.47 (d, J=7.0 Hz, ~99H).

DOPE-DOTA. Diacylphosphatidylethanolamine (DOPE) (12 mg, 0.016 mmol) was suspended in dry dichloromethane (~3 mL), followed by addition of DOTA-NHS (~18 mg, 0.036 mmol) and triethyl amine (50 µL). The reaction was continued for ~2.5 days at r.t., where after kaisertest (negative) and MALDI-TOF of reaction mixture indicated completion. The solvent was removed in vacuuo, and the crude mixture was dissolved in MeOH:H$_2$O 40:60 and purified by preparative HPLC (Xterra C8 column, MeCN/H$_2$O/TFA system. Gradient: 50->100% MeCN in 10 minutes). Yield: 13.5 mg, 74%. $^1$H NMR (400 MHz, Chloroform-d) δ 7.93 (s, 1H), 5.39-5.28 (m, 5H), 5.21 (dddd (br), J=5.6, 3.0 Hz, 1H), 4.21 (dd, J=12.0, 3.1 Hz, 1H), 4.32 (dd, J=12.1, 6.8 Hz, 2H), 4.11-4.01 (m, 2H), 3.89 (t, J=6.4 Hz, 2H), 3.49 (dd, J=14.6, 7.3 Hz, 8H) 3.09 (dd, J=14.6, 7.3 Hz, 15H), 2.63 (s, 7.5 Hz, 6H), 2.25 (dt, J=10.0, 7.5 Hz, 4H), 1.97 (q, J=6.4 Hz, 8H), 1.40-1.13 (m, ~42H), 0.84 (t, 6H). MALDI-TOF MS: Calc [M+H]$^+$: Calc 1131.45, Found: 1131.5.

Formulation

The carbohydrate materials as well as the Gd-chelating PLA, PLA-RhB and DOPE-DOTA were used after the synthesis described under the organic synthesis section. DOPE-RhB, DOPE-CF and BSA-DTPA(Gd) were purchased from Avanti Polar Lipids, INC. Absolute EtOH (99%) was purchased from CCS Healthcare. Glycerol trihexanoate (GTH) was purchased from CHEMOS GmbH. PBS was purchased from Fischer Scientific ((Dulbecco's Phosphate buffer saline. Without calcium, magnesium and phenol red). XSAIB (CT-contrast agent) was kindly provided by Nanovi Radiotherapy. All other additives (triglycerides and solvents) were purchased from Sigma Aldrich. All compounds were used as received from the manufacturer.

Preparation of Formulations Containing DOPE-RhB or DOPE-CF

DOPE-RhB was dissolved in EtOH or triglycerides and added to the formulations in amounts resulting in the desired final concentrations (~1.3*10$^{-3}$ ug/uL) in formulations consisting of lactose acetate:propionate 1:1/lactose isobutyrate co-formulated with either 25 wt % EtOH or 40 wt % triglyceride (GTO/GTH), with or without 10 wt % EtOH or 5 wt % PC (~240 uL formulations in total). The DOPE-RhB solutions were made from a motherstock of 1 mg/mL DOPE-RhB in EtOH with serial dilution into EtOH/triglyceride (GTO/GTH). The injected formulations were imaged in PBS in 8-well microscope slides under the confocal microscope.

DOPE-CF was dissolved in EtOH or triglycerides in concentrations of 1 mg/mL. ~10 uL of this stock was added to ~230 uL carbohydrate formulation to give concentrations of 0.042 ug/uL in formulations consisting of lactose acetate:propionate 1:1/lactose isobutyrate co-formulated with either 25 wt % EtOH or 40 wt % triglyceride (GTO/GTH), with or without 10 wt % EtOH or 5 wt % PC. The formulations were imaged in PBS in 8-well microscope slides under the confocal microscope.

Preparation of PLA-RhB Formulations

PLA-RhB (Mn~3000) was dissolved in EtOH in concentrations of 5 mg/mL and diluted 100 times into triglyceride (GTH or GTO). ~30 uL of this solutions were added to ~210 uL carbohydrate formulation to give concentrations of ~0.0063 ug/uL in formulations consisting of lactose acetate:propionate 1:1/lactose isobutyrate co-formulated with 40 wt % triglyceride (GTO/GTH) with or without 10 wt % EtOH or 5 wt % PC. The formulations were imaged in PBS in 8-well microscope slides under the confocal microscope.

Preparation of Formulations Containing Gd-Chelating Molecules

Carbohydrate esters (45 wt %) and XSAIB (10 wt %) were weighed off into a glass vial, followed by addition of tBuOH:water solutions of the Gd-chelator in the wanted concentrations after finished freeze-drying and formulation (3 mM, 1.5 mM, 0.75 mM and 0.3 mM). Aqueous solutions of GdCl$_3$ were also added to give the same concentrations of both chelator and Gd in the finished materials. The solutions were freeze-dried overnight and subsequently mixed GTH (40 wt %), and PC (5 wt %) applying ultrasonication (typically at 40-60° C.) and vortexing until homogeneiety. The formulations were either used the same day or later after a bit of ultrasonication/vortexing to assure homogeneity.

Confocal Microscopy

Laser Scanning Confocal Microscopy was performed using a Leica TCS SP5 Scanning Laser Confocal Microscope operated using a 61× wet objective and a 561 nm excitation DPPS Laser. Samples (~5-10 uL) were prepared in 8 well microscope slides containing PBS buffer and imaged on the same day to study the distribution of fluorescence signal within the material. In case of Rhodamine B, emission was detected between 575 and 674 nm, while in case of carboxy fluorescein emission was detected between 480 and 580 nm. Multiple images were acquired for each sample and z-stack images were acquired with a 0.5 um spacing between frames. Image processing, including 3D reconstruction and z-stack projections, was performed using FIJI.

In-Vitro MRI Scans

~100 uL of carbohydrate formulations were scanned in PBS buffer (2 mL glass vials) after formation using a PharmaScan 7T micro MRI scanner. All in-vitro MRI scans were conducted with a 3D mouse volume coil (Bruker RF volume coil with 3 cm inner diameter).

T1 RARE Imaging $T_1$ weighted images were obtained by $T_1$ weighted RARE imaging utilizing the following settings: Flip angle: 90°. TR: 1000 ms. TE: 6.8 ms. Echo spacing: 6.8 ms, averages: 7, repetitions: 7. Rare factor: 2. Slice thickness: 0.7 mm, slice package of 8 slices was generally applied. FOV: 20×20 mm². Image size: 256×256 voxels.

In-Vivo MRI Scans

~50-100 uL of carbohydrate formulations were injected subcutaneously on the hip area of NMRI Nude mice. For intramuscular injection, ~25 uL were injected in the thigh area. Pain relief was not necessary, and the injected mice moved around without problems. The mice were MRI scanned at specific timepoints post injection (same day, 1 day, 1 week, 3 weeks (PLA-formulations only)) using a PharmaScan 7T micro MRI scanner. All in-vivo MRI scans were done with a surface coil (Bruker RF surface coil, with a diameter of 2 cm).

T1 RARE Imaging

In-vivo $T_1$ weighted images were obtained by $T_1$ weighted RARE imaging utilizing the following settings: Flip angle: 90°. TR: 1500 ms, TE: 8 ms, Echo spacing: 8 ms, averages: 2, repetitions: 1, Rare factor: 4. FOV: 35×35 mm². Image size: 256×256 voxels. Slice thickness: 0.7 mm, slice packages of ~9-16 slices, depending on the volume of injected material, were applied.

T1 RARE Mapping $T_1$ values were obtained using saturation recovery experiments performed with a T1 map RARE sequence and 0.7 mm slices (package of 5-16 slices depending on size and shape of injected material). Flip angle: 90°. TR's: 5500, 4000, 3000, 1500, 800, 400 and 200 ms. TE: 7.5 ms averages: 2, repetitions: 1. FOV: 35×35 mm², collected into a matrix of 192×192 voxels.

Image data processing and extraction of $T_1$ from maps was performed on ParaVision software version 6.0.1. $T_1$ maps were performed using a nonlinear least square algorithm provided by the Image Sequence Analysis (ISA) tool of ParaVision.

Results and Discussion

Formulation of the injectable materials containing fluorophore labeled lipids or polymers were done by mixing the carbohydrate (lactose octaacetate:octapropionate 1:1 or lactose octaisobutyrate), triglyceride (glycerol trihexanoate (GTH) or glycerol trioctanoate (GTO)) containing dissolved fluorophore functionalized material and eventual co-solvent (propylene carbonate (PC) or ethanol (EtOH)) followed by ultrasonication until homogeneity. Loading of Gd and Gd chelating polymers or lipids in similar formulations was done by addition of aqueous solutions of these to the polymer material followed by freeze-drying and the addition of triglyceride and solvent as described above. While the carbohydrate confers structure to the material, the triglyceride ensures the required softness for diffusion and the added co-solvent helps enable diffusion of the added polymer/lipid to the material interface.

In order to easily visualize which molecular structures were capable of diffusing to the rim of the materials after injection and possibly provide $T_1$ contrast, formulations of fluorophore-functionalized lipids and polymers were examined in-vitro by confocal microscopy after injection into PBS. The best performing constructs were then functionalized with Gd-chelating moieties (DOPE/DTPA) and MRI scanned in-vitro (in PBS) or in-vivo (s.c. or intramuscular injection in mice) using a T1 RARE sequence. The relaxativity of formulations with the highest contrast was measured by T1 RARE mapping.

Fluorophore labeled amphiphilic lipids (DOPE derivatives of Carboxy Fluorescein (CF) or Rhodamine B (RhB)) were co-formulated with lactose esters and different additives (See materials and methods). Formulations based lactose octapropionate:octaaccetate 1:1 (LAP) or lactose isobutyrate (LI) and EtOH (25 wt %) displayed aggregated lipid particles throughout the matrix, which would result in non-uniform contrast. The formulation based on LAP and GTH (40%) displayed a uniform distribution of aggregated RhB-lipid which would result in a lack of exposure of the majority of the Gd-chelates to water and poor MRI contrast. However slight changes in the LAP: GTH formulation by addition of a co-solvent (5% PC or 10% EtOH) resulted in a clearly higher distribution of DOPE-RhB and DOPE-CF in the rim of the injected formulation (FIG. 2), as diffusion to the rim was facilitated by diffusion of solvent. The same result was seen with the LI+40% GTO-based formulation. The mixture of the 40% GTO and LI provides a highly hydrophobic environment in which the lipid tails are highly soluble, and the softness of the material makes diffusion to the rim easy.

The formulations seen in FIG. 2 were reconstructed with the two Gd-chelating lipids, DOPE-DOTA (Gd) and BSA-DTPA(Gd), as it was hypothesized on the basis of the confocal microscopy experiments, that formulations of similar Gd-chelating constructs would diffuse to the rim of the materials resulting in MRI $T_1$ contrast. Maximum ~3 mM of Gd-chelating lipid could be achieved in the formulations due to solubility limitations. The in-vitro (PBS) and in-vivo (s.c. injection of mice) results of the formulations are seen in FIGS. 3 and 4. As seen in FIG. 3, BSA-DTPA(Gd) formulations produced a bright rim in both in-vitro and in-vivo, however DOPE-DOTA(Gd) produced a brighter rim, probably due to DOTA being a more powerful chelator leading to a shorter $T_1$ (~410 ms in the material rim of DOPE-DOTA (Gd) vs ~1188 ms of BSA-DTPA(Gd) in the material rim in-vivo, day 1) (See table of $T_1$ relaxation times in supporting information). Both formulations, however, displayed clear leakage of Gd-chelating lipid into the subcutaneous compartment at day 7 (seen by increased bright area in the tissue around the injected material compared to day 1), which lead to decreased soft-tissue resolution. Smaller concentrations of Gd-chelating lipids were therefore tested with DOPE-DOTA(Gd) formulations (FIG. 4). All visible concentrations of DOPE-DOTA(Gd) resulted in clear leakage of lipid to the subcutaneous compartment, impairing soft tissue resolution. Hence Gd-lipid based formulations were abandoned as MRI markers. Instead, formulations containing Gd-chelating PLA constructs were investigated to determine their contrast and stability in-vitro and in-vivo.

FIG. 5 shows confocal microscopy images after injection into PBS of PLA-RhB (Mn 3000 Da) co-formulated with the same components which worked well for the DOPE-fluorophores: LAP 1:1, 40% GTH+5% PC and LI, 40% GTO. The LI, 40% GTO formulation performs better in terms of uniform situation of PLA-RhB in the rim of the material, while the LAP, 40% GTH, 5% PC formulation provides less uniform situation of the RhB-polymer in the rim, with more accumulation in the interior of the material. Both formulations display the same tendencies a week after injection, showing a relatively high stability of these formulations. Therefore, PLA-DOTA/DTPA (Gd) formulations were subsequently investigated as MRI contrast agents. MRI in-vitro and in-vivo results of PLA-DTPA(Gd) and PLA-DOTA(Gd) (~3 mM) formulated in the LAP 1:1, 40% GTH, 5% PC matrix are shown in FIG. 6. It was not possible to formulate Gd-chelating polymers or lipids in the LI, 40% GTO matrix due to precipitation in the formulations, therefore only the LAP based formulation was investigated. The PLA-DOTA (Gd) formulation created a broad, more diffuse rim, hard to distinguish from the subcutaneous fat, while the PLA-DTPA (Gd) formulation resulted in a thin, sharp rim easily distinguishable from the subcutaneous fat. The reason for the difference in quality of the MRI images of the two formulations is not clearly known, however the different shape and hydrophilicity of the chelating "head group" could influence diffusion properties of the chelate as well as influence packing of the polymer on the surface of the injected material.

Stability of the PLA-DTPA(Gd) formulation in terms of shape and contrast enhancement, was investigated further both subcutaneously (s.c.) with different concentrations of the chelate, and intramuscularly with the best performing concentration, compared with a blank (FIG. 7). The 3 mM PLA-DTPA(Gd) formulation displays a clear white rim both subcutaneously and intramuscularly, retaining contrast relatively well over the full study period of 3 weeks. The lower concentrations were relatively difficult to visualize and clearly distinguish from the subcutaneous fat on MRI, although their rim seemed to have a slightly higher $T_1$ contrast enhancement than the rim of the blank material (formulated 3 mM PLA without Gd). The high triglyceride content gives the marker a very soft texture, which makes it prone to shape changes over time, especially in moving muscle tissue, where fragmentation of the material was observed probably also associated with the higher pressure and complexity of muscle tissue compared to the s.c. compartment. The fragility of the formulation can be modulated by lowering the triglyceride content, creating a more stable material. Finally, to improve relaxativity, polymers (PLA/PLGA) with multiple Gd-chelation sites can be synthesized and added to the formulation instead of polymers with only one chelation site. This improvement will likely increase $T_1$ relaxation at the rim of the material creating a clearer, more defined contrast between the interior material, the rim and the surrounding tissue.

In-vivo relaxativity of the PLA-DTPA(Gd) formulations imaged in FIG. 7 along with $T_1$ contrast level over time of the 3 mM formulation (s.c.) is shown in FIG. 8. Due to only one concentration being efficient in enhancing $T_1$ contrast, relaxativity is very small, i.e. 0.159+−0.024 mM$^{-1}$S$^{-1}$. As a comparison, an injectable contrast agent based on Gd-chelating polysaccharide nanogels engineered by Chan et al [39], has a relaxativity of 5.4 mM$^{-1}$s$^{-1}$ at 7T, far superior in relaxativity to due to the polyfunctional Gd-chelaton sites and high water content of the material. The hydrophobic material with limited diffusion of polymer to its surface as well as mono-functionalization of PLA with Gd-chelator are the major reasons why the PLA-DTPA(Gd)-formulations from FIG. 7 display a low relaxativity. The 3 mM PLA-DTPA(Gd) formulation however displays a fairly short $T_1$ of ~877 ms 1 week post injections, a value which only changes slightly throughout the monitoring period. In comparison, the blank material-rim displayed a $T_1$ of ~1400 ms, and the surrounding tissue (s.c. or muscle) had an average $T_1$ of ~2600 ms. In order for the contrast enhancement to be observable in a clinical setting, the product of relaxativity and concentration (r1·[C]) in the equation $$\frac{1}{Ti} = \frac{1}{T0} + r1 \cdot [C]$$

needs to give at least 10% of the inherent relaxation rate (1/$T_0$) of the blank material and of the surrounding tissue [21]. The 3 mM formulation gives a r1·[C] of ~0.5s$^{-1}$, i.e. ~67% of the inherent $T_1$ relaxation rate of the blank material and ~124% of the inherent relaxation rate of the surrounding tissue, so observable contrast is clinically possible. The bright rims around the injected 3 mM formulations were in average measured to be around ~1 mm in diameter, and resolutions up to 0.33 mm$^3$ can be achieved on clinical 3T MRI scanners, even with short scan times [22]. Hence, the 3 mM PLA-DTPA(Gd) does display promising results in stability of contrast and contrast enhancement even for use in a clinical setup.

SPECIFIC EMBODIMENTS OF THE PRESENT INVENTION

Below some specific embodiments are listed.

According to one embodiment of the present invention, the clear contrast distinction is bright vs dark in two different phases of the composition after administration into the human or animal body. This is further seen in the figures.

According to yet another embodiment of the present invention the composition is intended for combined MR and CT imaging, and where the composition is arranged to provide a clear distinction between CT contrast and MRI contrast in a marker. As one example, CT may be only be seen in the dark MR area.

Furthermore, according to one embodiment of the present invention, the composition is a liquid before administration into the human or animal body that increases in viscosity by more than 10,000 centipoise (cP) after administration into the human or animal body. Moreover, the composition may be arranged to be a liquid before administration and with the ability to transform into a gel-like material after administration. Furthermore, the composition may be provided to become a solid material after administration, such as a crystalline or amorphous solid.

Moreover, according to yet another specific embodiment of the present invention, said at least one imaging contrast agent is more concentrated on the surface of the administered material after administration than inside the administered material for at least 1 hour to 3 months after administration, such as for at least 4 hours to 1 month, such as for at least 1 day to 2 months, such as for at least 2 days to 3 months after administration. In another embodiment, said at least one imaging contrast agent is more concentrated less than 1 cm away from the administered material after administration than inside the administered material for at least 1 hour to 3 months after administration, such as for at least 4 hours to 1 month, such as for at least 1 day to 2 months, such as for at least 2 days to 3 months after administration.

Furthermore, according to one embodiment of the present invention, an increase in viscosity after administration into the human or animal body is due to diffusion of a solvent-like molecule out of the administered material and into surrounding tissue.

According to one specific embodiment of the present invention, the non-water soluble carbohydrates are disaccharides with structures selected from:

Formulae:

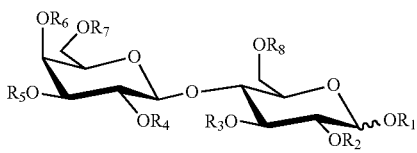
I

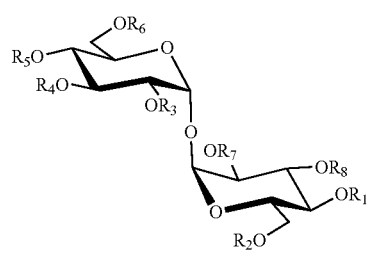
II

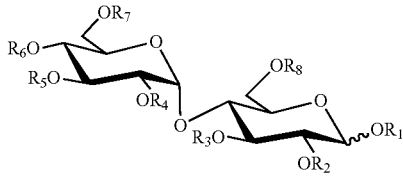
III wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

According to yet another embodiment, the non-water soluble carbohydrates are trisaccharides with structures selected from:

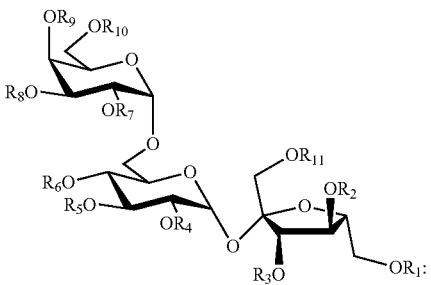
Formulae IV wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

At least 50% of the non-water soluble carbohydrates may be mono- or oligosaccharides containing at least one amino sugar unit. Moreover, according to another embodiment, the amino sugar has the structure:

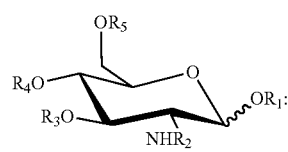
Formulae V wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, and mono-, di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of anomers such as α- and β-anomer centres of the above mentioned structural variations are claimed.

According to one specific embodiment, the non-water soluble carbohydrates comprises poly(ethylene glycol-b- caprolactone) (PEG-PCI), sucrose acetate isobutyrate (SAIB), poly(D,L-lactic acid), or poly(lactic-co-glycolic acid) (PGLA), or a combination thereof. According to another embodiment, the non-water soluble carbohydrates comprise mixed saccharides of furanose and pyranose.

Moreover, according to one specific embodiment of the present invention, said at least one imaging contrast agent makes the composition visible by PET imaging, SPECT imaging, Ultrasound imaging, CT imaging, MR imaging, x-ray imaging, fluoroscopy imaging, fluorescence imaging, or OCT imaging.

Moreover, according to yet another embodiment, the composition contains two imaging contrast agents that are visible by at least two imaging methods, such as visible by at least two imaging methods chosen from PET imaging, SPECT imaging, Ultrasound imaging, CT imaging, MR imaging, x-ray imaging, fluoroscopy imaging, fluorescence imaging, or OCT imaging.

Furthermore, according to one embodiment of the present invention the composition contains an imaging contrast agent for CT imaging and an imaging contrast agent for MR imaging.

According to one specific embodiment of the present invention, the composition contains an MR imaging contrast agent containing Gadolinium associated with a chelate. The composition may contain an MR imaging contrast agent containing Gadolinium associated with a chelate that is covalent linked to a polymer. Moreover, the composition may contain an MR imaging contrast agent containing Gadolinium associated with a chelate that is covalent linked to poly lactic acid (PLA). Moreover, the composition may contain an MR imaging contrast agent containing Gadolinium associated with a chelate chosen from PLA-DTPA or PLA-DOTA polymer chelates. Furthermore, the composition may contain a CT contrast agent and an MR imaging contrast agent containing Gadolinium associated with a chelate, and wherein the CT contrast agent is hydrophobic. As mentioned before, the hydrophobic CT contrast agent may be relatively uniformly distributed throughout the whole formulation, and the amphiphilic Gd-chelating constructs are capable of diffusing to the rim.

According to one embodiment, the composition comprises a pharmacologically active compound that is released into the surrounding tissue, such as chemotherapy that enhances the effect of radiotherapy.

Furthermore, according to yet another specific embodiment the composition is intended to be administered to the human or animal body through a syringe, an endoscope or a bronchoscope to the target tissue preferably wherein the composition after insertion into the human or animal body constitutes a medical or surgical implant for tissue or surgical adhesion which preferably is wound dressing, a hemostat, enhances tissue regeneration, is a void filler.

The present invention also embodies a medical or surgical implant comprising a composition according to the present invention, wherein the composition is part of a sprayable composition.

Moreover, the present invention provides a composition system which may be used as a tissue marker for guided surgery and/or imaging by one or multiple imaging modalities. The composition system may allow for detection of the tissue marker by an external imaging modality if administered or implanted into a mammalian body. Exemplary external imaging modalities include, but are not limited to, X-ray imaging, such as CT imaging, MRI, PET imaging, single photon emission computed tomography (SPECT) imaging, nuclear scintigraphy imaging, ultrasonography imaging, ultrasonic imaging, near-infrared imaging and/or fluorescence imaging.

EXAMPLES

Example 1: Synthesis of Carbohydrate Esters

General experimental conditions: All reactions were carried out under inert atmosphere ($N_2$). Water sensitive liquids and solutions were transferred via syringe. Water used for washing of the isolated products was in all cases MilliQ water. Organic solutions were concentrated by rotary evaporation at 30-60° C. at 200-0 mbar. Thin layer chromatography (TLC) was carried out using aluminum sheets pre-coated with silica 60F (Merck 5554). The TLC plates were inspected under UV light or developed using a cerium ammonium sulphate solution (1% cerium (IV) sulphate and 2.5% hexa-ammonium molybdate in a 10% sulfuric acid solution).

Reagents: DOTA-NHS was purchased from Macrocyclics. All other chemicals were purchased from Sigma Aldrich and were used as received. Dry pyridine was obtained by drying over molecular sieves (4 Å) for 2-3 days prior to use.

Instrumentation: Nuclear Magnetic Resonance (NMR) was conducted on a Bruker Ascend™ 400 MHz—operating at 401.3 MHz for $^1$H and 100.62 MHz for $^{13}$C—with a 5 mm H—Broadband Dual Channel z-gradient Prodigy cryoprobe at 298 K using the residual solvent as internal standard. All coupling constants (J) are expressed in Hz. The FID files were processed in Mnova Suite. In $^1$H-NMR spectra of α,β anomeric mixtures, the integral of H-1 of the most abundant anomer was always set to 1.0, and the percentage of each anomeric species was calculated from the integral ratio of H-1 α and H-1 β. MALDI-TOF MS was conducted on a Bruker Autoflex Speed™ mass spectrometer. The matrix used for MALDI-TOF was a mixture of 2,5 dihydroxy benzoic acid (DHB) spiked with sodium trifluoroacetate in ethanol (60 mg/mL).

General Experimental Procedure for Synthesis of Carbohydrate Esters

Lactose (typically 10-100 g) was suspended in dry pyridine under inert atmosphere ($N_2$). Hereafter, acetic, propionic or isobutyric anhydride (2.2 eq. pr. hydroxyl group) was carefully added. Then, a catalytic amount of DMAP (0.1 eq.) was added. The reactions were heated to 48° C. overnight, and then continued for ~24 hours at room temperature, until TLC and MALDI-TOF showed complete acylation of the starting material. The reactions were concentrated under reduced pressure and co-evaporated with toluene. The concentrates were dissolved in $CHCl_3$ and washed with $NaHCO_3$(aq.) (5×), brine (1×) and water (1×). The organic phases were dried with $MgSO_4$ (s), filtered, concentrated under reduced pressure and dried in vacuo. Yields and reported spectra of individual sugar esters can be found below.

α,β Lactose Octaacetate

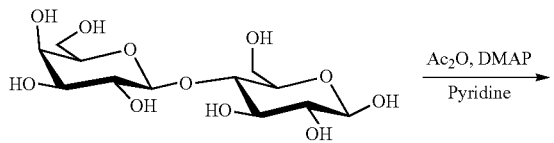

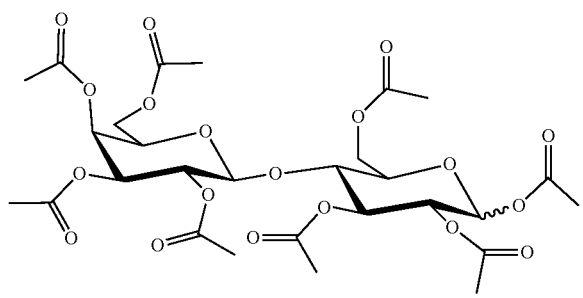

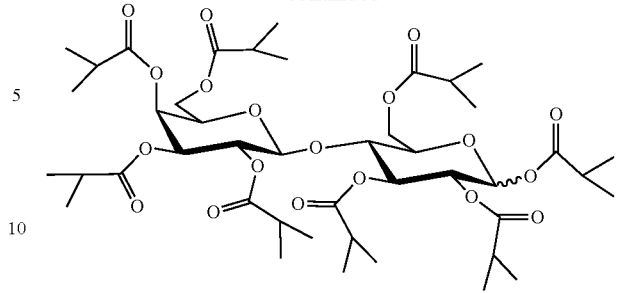

Yield: 93.7% yield (mixture of anomers: ~30% α and ~70% β). $^1$H-NMR: (400 MHz, Chloroform-d) δ 6.24 (d, J=3.7 Hz, 1H, H-1 α), 5.66 (d, J=8.3 Hz, 1H, H-1 β), 5.44 (dd, 10.28, 9.53 Hz, 0.4H), 5.37-5.31 (m, 2H), 5.23 (t, J=9.1 Hz, 1H), 5.15-5.00 (m, 3H), 4.99-4.91 (m, 2H), 4.50-4.41 (m, 3H), 4.17-4.05 (m, 4H), 3.99 (ddd, J=10.2, 4.3, 2.1 Hz, 0.4H, H5 α), 3.91-3.78 (m, 3H), 3.75 (ddd, J=9.9, 4.8, 2.0 Hz, 1H, H5 β), 2.19-1.93 (singlets, ~32H, CH$_3$ acetyls). MALDI TOF-MS: Calc [M+Na]$^+$: 701.59. Found: 701.51.

α,β Lactose Octapropionate

Yield: 89.5% (mixture of anomers: ~30% α and ~70% β). $^1$H NMR (400 MHz, Chloroform-d) δ 6.26 (d, J=3.8 Hz, 1H, H-1α), 5.68 (d, J=8.3 Hz, 1H, H-1β), 5.48 (dd, J=10.3, 9.3 Hz, 0.4H), 5.40-5.34 (m, 2H), 5.27 (t, J=9.5 Hz, 1H), 5.18-5.00 (m, 3H), 5.03-4.91 (m, 2H), 4.50-4.41 (m, 3H), 4.24-4.02 (m, ~4H), 3.95 (ddd, J=10.1, 3.8, 1.7 Hz, 0.4H, H5 α), 3.91-3.80 (m, 3H), 3.70 (ddd, J=9.9, 4.5, 2.0 Hz, 1H, H5 β), 2.70-2.32 (m, ~11H), 1.26-1.01 (m, ~68H). MALDI TOF-MS: Calc [M+Na]$^+$: 926.02. Found: 925.70.

Example 2: Synthesis of Fluorescently Labeled PLA

PLA-RhB

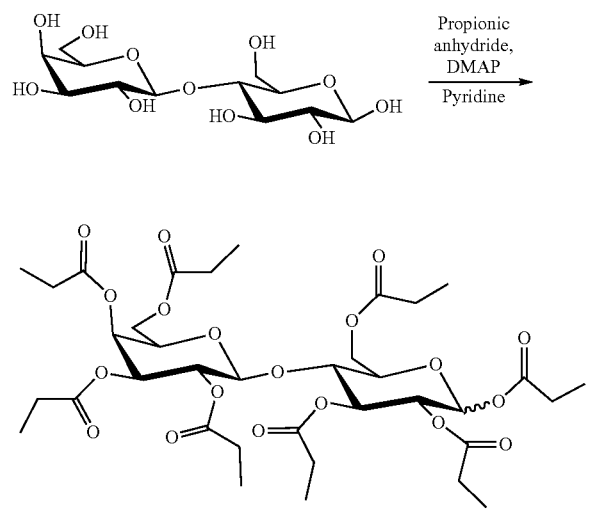

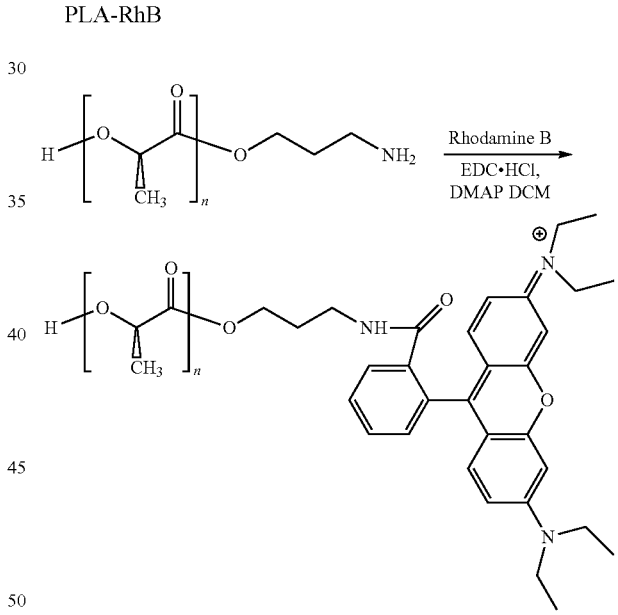

Yield: 84% (mixture of anomers: ~30% α and ~70% β). $^1$H-NMR (400 MHz, Chloroform-d) δ 6.26 (d, J=3.7 Hz, 1H, H1-α), 5.68 (d, J=8.3 Hz, 1H, H-1 β), 5.47 (dd, 10.3, 9.2 Hz, 0.4H), 5.38-5.33 (m, 2H), 5.26 (t, J=9.2 Hz, 1H), 5.15-5.00 (m, 3H), 5.02-4.91 (m, 2H), 4.49-4.41 (m, 3H), 4.15-4.03 (m, 4H), 3.98 (ddd, J=10.1, 3.9, 1.8 Hz, 0.4H, H5 α), 3.91-3.77 (m, 3H), 3.73 (ddd, J=9.9, 4.6, 2.0 Hz, 1H, H5 β), 2.47-2.15 (m, ~23H), 1.19-0.99 (m, ~34H). MALDI TOF-MS: Calc [M+Na]$^+$: 813.80. Found: 813.42.

α,β Lactose Octaisobutyrate

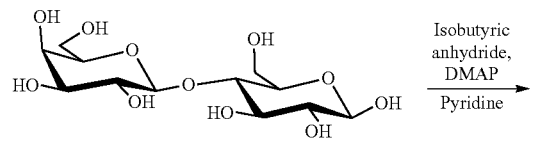

PLA-NH$_2$ (Mn~2500) (260 mg, 0.1 mmol) was suspended in dry DCM (~5 mL). Then, a pre-mixed mixture of Rhodamine-B (105, 0.2 mmol), EDC-HCl (80 mg, 0.4 mmol) and DMAP (106 mg, 0.9 mmol) dissolved in 5 mL dry DCM was added, and the reaction was continued at r.t. for 2 days, where Kaiser test was negative, indicating full functionalization. The solvents were removed in vacuo, and the crude mixture was dissolved in DMSO and purified by dialysis (Mw cutoff: 1000 da) against MQ water for 14 days. Yield: 299 mg (97%). $^1$H NMR (400 MHz, DMSO-d$_6$) δ 8.31 (d (br), J=7.7 Hz, 1H), 7.95 (br. t, J=7.4 Hz, 1H), 7.87 (br. t, J=7.6 Hz, 1H), 7.57-7.44 (m, 2H), 7.05-7.00 (m, 1H), 6.39-6.24 (m, ~5H), 5.20 (q, J=7.1 Hz, ~33H), 3.65 (dd (br), J=13.8, 6.9 Hz, 4H), 3.31 (br. q, J=7.1 Hz, 8H), 3.12-2.94 (m, 2H), 1.47 (d, J=7.1 Hz, ~99H), 1.08 (t, J=6.9 Hz, 12H).

Example 3: Synthesis of Gd-Chelators

DOPE-DOTA

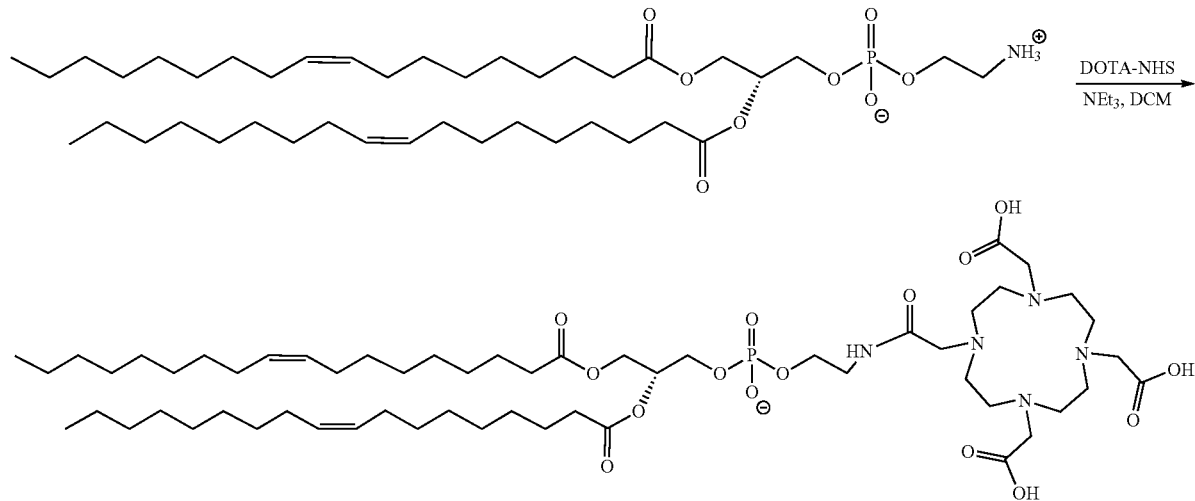

Diacylphosphatidylethanolamine (DOPE) (12 mg, 0.016 mmol) was suspended in dry dichloromethane (3 mL), followed by addition of DOTA-NHS (~18 mg, 0.036 mmol) and triethyl amine (50 µL). The reaction was continued for 2.5 days at r.t., where after kaisertest (negative) and MALDI-TOF of the reaction mixture indicated completion. The solvent was removed in vacuo, and the crude mixture was dissolved in MeOH:H$_2$O 40:60 and purified by preparative HPLC (Xterra C8 column, MeCN/H$_2$O/TFA system. Gradient: 50→100% MeCN in 10 minutes). Yield: 13.5 mg, 74%. $^1$H NMR (400 MHz, Chloroform-d) δ 7.93 (s, 1H), 5.39-5.28 (m, 5H), 5.21 (dddd (br), J=5.6, 3.0 Hz, 1H), 4.32 (dd, J=12.0, 3.1 Hz, 1H), 4.09 (dd, J=12.1, 6.8 Hz, 1H), 3.95-3.78 (m, 4H), 3.49 (dd, J=14.6, 7.3 Hz, 8H) 3.09 (dd, J=14.6, 7.3 Hz, ~15H), 2.63 (s, 4H), 2.25 (dt, J=10.0, 7.5 Hz, 4H), 1.97 (q, J=6.4 Hz, 8H), 1.40-1.13 (m, ~40H), 0.84 (t, 6H). MALDI-TOF MS: Calc [M+H]$^+$: Calc 1131.45, Found: 1131.5.

PLA-DTPA

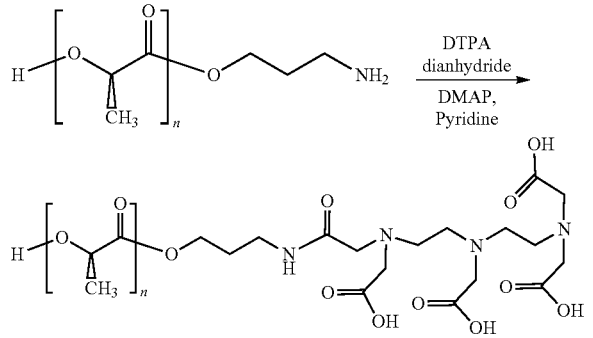

PLA-NH$_2$ (Mn~2500) (260 mg, 0.1 mmol) was suspended in dry pyridine (10 mL) followed by addition of DTPA-dianhydride (57.5 mg, 0.16 mmol) and a catalytic amount of DMAP (1.3 mg, 0.01 mmol). The reaction was continued for 1.5 day, where Kaiser test (negative) indicated the reaction was completed. 5 mL MQ water was added and stirred for 2 h to hydrolyze any residual anhydride. The solvents were removed in vacuo, and the crude mixture was dissolved in DMSO and purified by dialysis (Mw cutoff: 1000 da) against MQ water for 10 days. Yield: 285 mg (96%). $^1$H NMR (400 MHz, DMSO-d$_6$) δ 8.09 (t, J=5.08 Hz, NH, ~1H), 5.20 (q, J=7.0 Hz, ~33H), 5.47 (s, 1H, OH), 4.21 (q, J=7.0 Hz, 2H), 4.17-4.01 (m, 2H)), 3.69-3.21 (m, 10H), 3.14 (q, J=7.0 Hz, ~2H), 3.06-2.81 (m, ~6H), 1.74 (p, J=7.0 Hz, 2H), 1.47 (d, J=7.0 Hz, ~99H).

PLA-DOTA

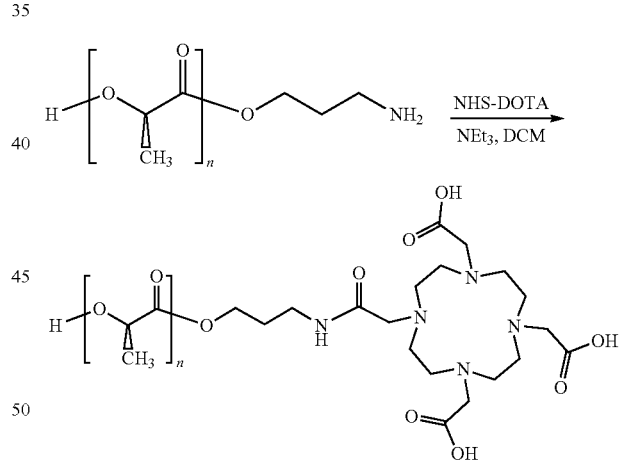

PLA-NH$_2$ (Mn~2500) (80 mg, 0.032 mmol) was suspended in dry dichloromethane (3 mL), followed by addition of DOTA-NHS (35 mg, 0.0704 mmol) and triethyl amine (40 µL). The reaction was continued for 2.5 days at r.t., where Kaiser test (negative) indicated completion. The solvent was removed in vacuo, and the crude mixture was dissolved in DMSO and purified by dialysis (Mw cutoff: 1000 da) against MQ water for 8-10 days. Yield: 89.6 mg (97%). $^1$H NMR (400 MHz, DMSO-d$_6$) δ 8.23 (s, NH, ~1H), 5.21 (q, J=7.0 Hz, ~33H), 4.21 (q, J=7.0 Hz, 2H), 4.16-3.99 (m, 2H), 3.49-3.34 (m, 6H), 3.24-3.03 (m, 4H), 3.03-2.87 (m, ~9H), 2.70-2.61 (m, 4H), 1.79 (p, J=7.0 Hz, 2H), 1.63 (d, J=7.1 Hz, 1H), 1.47 (d, J=7.0 Hz, ~99H).

Example 4: In-Vitro Confocal Microscopy of Markers Containing Fluorescent Amphiphiles Laser scanning confocal microscopy was conducted using a Leica TCS SP5 Scanning Laser Confocal Microscope (61× wet objective, 561 nm excitation DPPS Laser) on 5-10 uL volumes of different marker compositions (see Table 1) in PBS buffer in order to investigate distribution of fluorescently labeled amphiphiles in the markers. A predominant distribution to the marker rim indicates the possibility of primary contrast enhancement at the marker rim when formulating the corresponding Gd chelators. The markers were prepared in 8 well microscope slides containing PBS buffer and imaged the same day. Multiple images were acquired for each sample with a 0.5 um spacing between z-stack frames. Image processing was performed using FIJI. All formulations listed in Table 1 show predominant accumulation of fluorophore at the marker-water interface. Representative results are shown in FIG. 9.

TABLE 1

Specifications for preparation of fluorophore containing marker formulations.

| Formulation# | Composition (w/w %) | | | | Concentration (μg/μL) |
|---|---|---|---|---|---|
| | Sugar ester | Triglyceride | Solvent | | Fluoresc. Amphiphile |
| 1 | LAP 1:1 65 | GTH 40 | PC 5 | — | PLA-RhB 0.006 |
| 2 | LAP 1:1 50 | GTH 40 | PC — | EtOH 10 | PLA-RhB 0.006 |
| 3 | LOIB 60 | GTO 40 | PC — | EtOH — | PLA-RhB 0.006 |
| 4 | LAP 1:1 75 | GTH 20 | PC 5 | — | PLA-RhB 0.006 |
| 5 | LAP 1:1 65 | GTH 40 | PC 5 | — | DOPE-RhB 0.001 |
| 6 | LAP 1:1 50 | GTH 40 | PC — | EtOH 10 | DOPE-RhB 0.001 |
| 7 | LOIB 60 | GTO 40 | PC — | EtOH — | DOPE-RhB 0.001 |
| 8 | LAP 1:1 65 | GTH 40 | PC 5 | — | DOPE-CF 0.04 |
| 9 | LAP 1:1 50 | GTH 40 | PC — | EtOH 10 | DOPE-CF 0.04 |
| 10 | LOIB 60 | GTO 40 | PC — | EtOH — | DOPE-CF 0.04 |

LAP 1:1: Lactose octaacetate:octapropionate 1:1.
LOIB: Lactose octaisobutyrate.
GTH: Glycerol trihexanoate.
GTO: Glycerol trioctanoate.
PC: Propylene carbonate.
EtOH: Ethanol.
PLA: Poly-(L-lactide).
DOPE: Diacylphosphatidylethanolamine,
RhB: Rhodamine B.
CF: Carboxy fluorescein.

Example 5: In-Vitro MRI Imaging of Markers

Single markers (~50 μL) containing 3 mM concentrations of different Gd-chelators (see Table 2) were injected into 2 mL glass vials containing PBS buffer and investigated using a PharmaScan 7T micro MRI scanner by T1 RARE imaging (Flip angle: 90°. TR: 1000 ms. TE: 6.8 ms. Echo spacing: 6.8 ms, averages: 7, repetitions: 7. Rare factor: 2. Slice thickness: 0.7 mm, slice package of 8. FOV: 20×20 mm$^2$. Resolution: 256×256 voxels) in order to visualize T1 enhancement at the marker-water interface. The markers were MRI scanned while still in the PBS vials within 1 week after injection. All scans were conducted using a 3D mouse volume coil (Bruker RF volume coil with 3 cm inner diameter). Image data processing was performed on ParaVision software version 6.0.1. All markers displayed $T_1$ contrast enhancement at the marker-water interface. The results are shown in FIG. 10.

TABLE 2

Specifications for preparation of Gd-containing marker formulations for in-vitro MRI scan.

| Formulation# | Composition (w/w %) | | | | Concentration (mM) |
|---|---|---|---|---|---|
| | Sugar ester | Triglyceride | Solvent | CT contrast | Gd-chelator |
| 1 | LAP 1:1 45 | GTH 40 | PC 5 | x-SAIB 10 | BSA-DTPA(Gd) 3 |
| 2 | LAP 1:1 45 | GTH 40 | PC 5 | x-SAIB 10 | DOPE-DOTA(Gd) 3 |
| 3 | LAP 1:1 45 | GTH 40 | PC 5 | x-SAIB 10 | PLA-DTPA(Gd) 3 |
| 4 | LAP 1:1 45 | GTH 40 | PC 5 | x-SAIB 10 | PLA-DOTA(Gd) 3 |

LAP 1:1: Lactose octaacetate:octapropionate 1:1.
GTH: Glycerol trihexanoate.
PC: Propylene carbonate.
PLA: Poly-(L-lactide).
DOPE: Diacylphosphatidylethanolamine,
BSA: Bis(stearylamide).
DOTA: 1,4,7,10-tetra-azacyclododecane-1,4,7,10-tetraacetic acid.
DTPA: diethylenetriaminepentaacetic acid.
x-SAIB: 6,6'-di-triidobenzene-isobuturic-sucrose.

TABLE 3

In-vivo $T_1$ relaxation table of material rims formulated with the above listed species in the stated concentrations. Base formulation was in all cases the LAP 1:1, 40% GTH, 5% PC matrix.
In-vivo $T_1$ values

| mM PLA-DTPA(Gd) | T1 rim PLA-DTPA(Gd) (msec) | mM DOPE-DOTA(Gd) | T1 rim DOPE-DOTA(Gd) (msec) |
|---|---|---|---|
| 3 mM | 876.93 | 3 mM | 409.95 |
| 1.5 mM | 917.79 | 1.5 mM | 779.40 |
| 0.75 mM | 1089.45 | 0.75 mM | 942.46 |
| 0.3 mM | 1145.45 | 0.3 mM | 1212.26 |
| No Gd | 1421.35 | No Gd | 1677.27 |

| T1 rim BSA-DPTA(Gd), 3 mM (msec) | T1 rim PLA-DOTA(Gd), 3 mM (msec) |
|---|---|
| 1188.27 | 949.28 |

Example 6: In-Vivo CT and MRI Imaging of Subcutaneous Markers 6.1:

The formulations from Example 5 were injected in 50 μL volumes subcutaneously in the hind leg of NMRI Nude mice (n=1 for each formulation). The mice were MRI and CT scanned 1 day and 1 week post injection, utilizing the same scanners, software and coil as in Example 5. Both CT scan (Inveon small animal CT scanner (Siemens Medical Systems), processing performed on Inveon software), T1 RARE imaging (Flip angle: 90°. TR: 1500 ms, TE: 8 ms, Echo spacing: 8 ms, averages: 2, repetitions: 1, Rare factor: 4.

FOV: 35×35 mm². Resolution: 256×256 voxels. Slice thickness: 0.7 mm, slice packages of ~9-16 depending on marker size) and T1 RARE mapping (Flip angle: 90°. TR's: 5500, 4000, 3000, 1500, 800, 400 and 200 ms. TE: 7.5 ms, Echo spacing: 7.5 ms. Rare factor: 2. Averages: 2, repetitions: 1. FOV: 35×35 mm², collected into a matrix of 192×192 voxels, slice packages of ~9-16 depending on marker size) was performed, in order visualize the markers as well as measure the $T_1$ relaxation time at the marker rim. Data processing was performed on ParaVision software version 6.0.1. While the Gd-chelating lipids seemed to leak out of the marker over time, the Gd-chelating PLA analogues did not result in visible leakage but seemed to stay predominantly at the marker-water interface, causing a bright $T_1$ enhancement of the marker rims. The results from day 7 are shown in FIG. 11.

6.2:

The best performing formulation from FIG. 11, with the clearest contrast enhancement (FIG. 11 *a-b*. Formulation 3, Table 2), was, injected subcutaneously along with an additional formulation containing 20% triglyceride (see Table 4) in the hind leg of NMRI Nude mice (~50 μL volumes, n=4). The mice were then CT and MRI scanned at specific timepoints post injection (MRI: 1 day, 1 week, 2 weeks, 3 weeks, 4 weeks and 6 weeks. CT: week 1, 3 and 6) in order to assess marker volumes, as well as CT and MRI ($T_1$) contrast enhancement over time. The same scan methods, software and equipment as described in 6.1 was employed. All markers displayed $T_1$ enhancement and high CT contrast enhancement over the entire study period. After ended study, the mice were euthanized and the markers removed surgically, no visible irritation or inflammation was present around the markers. The results are shown in FIGS. 12.1 and 12.2.

TABLE 4

Specifications for preparation of Gd-containing marker formulations for 6-week study in-vivo of subcutaneous markers.

| Formulation# | Composition (w/w %) | | | | Concentration (mM) Gd-chelator |
|---|---|---|---|---|---|
| | Sugar ester | Triglyceride | Solvent | CT contrast | |
| 1 | LAP 1:1 45 | GTH 40 | PC 5 | x-SAIB 10 | PLA-DTPA(Gd) 3 |
| 2 | LAP 1:1 65 | GTH 20 | PC 5 | x-SAIB 10 | PLA-DTPA(Gd) 3 |

LAP 1:1: Lactose octaacetate:octapropionate 1:1.
GTH: Glycerol trihexanoate.
PC: Propylene carbonate.
PLA: Poly-(L-lactide).
DTPA: diethylenetriaminepentaacetic acid.
x-SAIB: 6,6'-di-triidobenzene-isobuturic-sucrose.

Example 7: In-Vivo CT and MRI Imaging of Intramuscular Marker

Formulation 1 from Table 4, Example 6.2 (25 μL) was injected into the thigh muscle of an NMRI Nude mouse to monitor marker stability in frequently moving tissue. The mouse did not show any signs of pain or difficulty moving around, the weight of the mouse also remained stable throughout the experiment. MRI scan was conducted 7 days post injection using the same scanner, T1 RARE scan method and coil as listed in Example 6.1. Image processing was performed on ParaVision software version 6.0.1. At 7 days post injection, CT scan of the marker was also performed on the same equipment as listed in Example 5-6. The MRI images showed $T_1$ enhancement at the marker rim. The results are shown in FIG. 13.

Conclusion

The lactose acetate:propionate 1:1 formulation containing 3 mM PLA-DTPA(Gd), 40% GTH and 5% PC performed well as dual MRI and CT marker over the observation period of 3 weeks. The stable $T_1$ contrast enhancement displayed sufficient strength and sufficient resolution making it amenable to be observable in patients when using standard clinical MRI facilities and setup. These agents have the potential to result in a novel, commercially applicable, injectable marker for treatment planning and monitoring during IGRT. Future development includes adjusting the triglyceride level and addition of polyfunctional Gd-chelating polymers to achieve both enhanced $T_1$ contrast as well as a stable 3D structure optimal for tracking in-vivo.

ABBREVIATIONS

BSA: Bis(Stearylamide)
CF: Carboxyfluorescein
CT: Computed Tomography
DOPE: Diacylphosphatidylethanolamine
DOTA: 1,4,7,10-tetra-azacyclododecane-1,4,7,10-tetraacetic acid.
DTPA: diethylenetriaminepentaacetic acid
EBUS: Endobronchial Ultrasound
EDC: 1-Ethyl-3-(3-dimethylaminopropyl) carbodiimide.
EtOH: Ethanol
EUS: Endoscopic Ultrasound
G: Gauge ("needle size")
GTH: Glycerol Trihexanoate
GTO: Glycerol Trioctanoate
IGRT: Image Guided Radiotherapy
LAP: Lactose octaacetate:octapropionate 1:1
LI: Lactose octaisobutyrate
MALDI-TOF: Matrix assisted laser desorption/ionization time-of-flight mass spectrometry.
MRI: Magnetic Resonance Imaging
PBS: Phosphate Buffered Saline
PC: Propylene Carbonate
PLA: Polylactic Acid
RARE: Rapid Acquisition with Relaxation Enhancement
RhB: Rhodamine B
RT: Radio Therapy
SAIB: Sucrose Acetate Isobutyrate
S.C.: Subcutaneous
T: Tesla
$T_1$: Longitudinal relaxation
$T_2$: Transverse relaxation
TE: Echo time
TLC: Thin Layer Chromatography
TR: Repetition Time
Wt %: Weight %
XSAIB: 6,6'-di-triidobenzene-isobuturic-sucrose or IodoSAIB

REFERENCES

[1]: Radiotherapy Risk Profile WHO/IER/PSP/2008.12
[2]: Baskar, R., Lee, K. A., Yeo, R., & Yeah, K. W. (2012). Cancer and radiation therapy: current advances and future directions. *Int J Med Sci,* 9(3), 193-199.
[3]: Goyal, S., & Kataria, T. (2014). Image Guided Radiation Therapy. *J Nucl Med Radiat Ther,* 5(179).

[4]: Zelefsky, M. J., Kollmeier, M., Cox, B., Fidaleo, A., Sperling, D., Pei, X., Carver, B., Coleman, J., Lovelock, M. & Hunt, M. (2012). Improved clinical outcomes with high-dose image guided radiotherapy compared with non-IGRT for the treatment of clinically localized prostate cancer. *International Journal of Radiation Oncology\* Biology\* Physics*, 84(1), 125-129.

[5]: Njeh, C. F. (2008). Tumor delineation: The weakest ink in the search for accuracy in radiotherapy. *Journal of Medical Physics*, 33(4), 136.

[6]: Luna, A., Vilanova, J. C., Da Cruz Jr, L. C. H., & Rossi, S. E. (Eds.). (2013). *Functional Imaging in Oncology: Biophysical Basis and Technical Approaches* (Vol. 1). Springer Science & Business Media, 12-13.

[7]: Gao, Z., Wilkins, D., Eapen, L., Morash, C., Wassef, Y., & Gerig, L. (2007). A study of prostate delineation referenced against a gold standard created from the visible human data. *Radiotherapy and oncology*, 85(2), 239-246.

[8]: Villeirs, G. M., Van Vaerenbergh, K., Vakaet, L., Bral, S., Claus, F., De Neve, W. J., Verstraete, K. L. & De Meerleer, G. O. (2005). Interobserver Delineation Variation Using CT versus Combined CT+ MRI in Intensity-Modulated Radiotherapy for Prostate Cancer. *Strahlentherapie and Onkologie*, 181(7), 424-430.

[9]: Bogdanov, A. & Mazzanti, M. L (2011), Molecular MR Contrast Agents for the Detection of Cancer: Past and Present. *Seminars in oncology* 38.1 42-54.

[10]: Jonsson, J. H., Garpebring, A., Karlsson, M. G., & Nyholm, T. (2012). Internal Fiducial Markers and Susceptibility Effects in MRI—Simulation and Measurement of Spatial Accuracy. *International Journal of Radiation Oncology\* Biology\* Physics*, 82(5), 1612-1618.

[11]: Parker, C. C., Damyanovich, A., Haycocks, T., Haider, M., Bayley, A., & Catton, C. N. (2003). Magnetic resonance imaging in the radiation treatment planning of localized prostate cancer using intra-prostatic fiducial markers for computed tomography co-registration. *Radiotherapy and oncology*, 66(2), 217-224.

[12]: Fuller, C. D., & Scarbrough, T. J. (2006). Fiducial markers in image-guided radiotherapy of the prostate. *US Oncological Disease*, 1, 75-9.

[13]: Jølck, R. I., Binderup, T., Hansen, A. E., Scherman, J. B., Munch of Rosenschold, P., Wr, A., & Andresen, T. L. (2014). Injectable colloidal gold in a sucrose acetate isobutyrate gelating matrix with potential use in radiation therapy. *Advanced healthcare materials*, 3(10), 1680-1687.

[14]: Rydhög, J. S., Jølck, R. I., Andresen, T. L., & of Rosenschöld, P. M. (2015). Quantification and comparison of visibility and image artifacts of a new liquid fiducial marker in a lung phantom for image-guided radiation therapy. *Medical physics*, 42(6), 2818-2826.

[15]: Szeto, A., Chin, L., Whelan, P., Wilson, J., & Lee, J. (2014). Image-guided radiation therapy using surgical clips for localization of colonic metastasis from thyroid cancer. *Radiation Oncology*, 9(1), 1.

[16]: http://nanovi.com/bioxmark/visibility/, link assessed 24.08 016

[17]: Zhou, Z., & Lu, Z. R. (2013). Gadolinium-based contrast agents for magnetic resonance cancer imaging. *Wiley Interdisciplinary Reviews: Nanomedicine and Nanobiotechnology*, 5(1), 1-18.

[18]: Kamaly, N., D Miller, A., & D Bell, J. (2010). Chemistry of tumour targeted T1 based MRI contrast agents. *Current topics in medicinal chemistry*, 10(12), 1158-1183.

[19]: Courant, T., Roullin, V. G., Cadiou, C., Callewaert, M., Andry, M. C., Portefaix, C. Hoeffel, C., de Goldstein, M. C., Port, M., Laurent, S., Elst, L. V., Muller, R., Molinari, M. & Chuburu, F., (2012). Hydrogels incorporating GdDOTA: towards highly efficient dual T1/T2 MRI contrast agents. *Angewandte Chemie International Edition*, 51(36), 9119-9122.

[20]: Chan, M., Lux, J., Nishimura, T., Akiyoshi, K., & Almutairi, A. (2015). Long-Lasting and Efficient Tumor Imaging Using a High Relaxivity Polysaccharide Nanogel Magnetic Resonance Imaging Contrast Agent. *Biomacromolecules*, 16(9), 2964-2971.

[21]: Dumas, S., Jacques, V., Sun, W. C., Troughton, J. S., Welch, J. T., Chasse, J. M., Schmitt-Willich, H. & Caravan, P. (2010). High relaxivity MRI contrast agents part 1: Impact of single donor atom substitution on relaxivity of serum albumin-bound gadolinium complexes. *Investigative radiology*, 45(10), 600.

[22]: Herrmann, K. H., Schmidt, S., Kretz, A., Haenold, R., Krumbein, I., Metzler, M., Gaser, C., Witte, O. W. & Reichenbach, J. R. (2012). Possibilities and limitations for high resolution small animal MRI on a clinical whole-body 3T scanner. *Magnetic Resonance Materials in Physics, Biology and Medicine*, 25(3), 233-244.

The invention claimed is:

1. A composition for at least MR imaging, comprising non-water soluble carbohydrates, wherein at least 50% of the non-water soluble carbohydrates are carbohydrates selected from derivatives of lactose, maltose, trehalose, raffinose, glucosamine, galactosamine, lactosamine, sucrose or derivatives of sucrose, or mixed saccharides, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, wherein the composition contains at least one imaging contrast agent, and wherein the composition provides a phase separation which provides a clear contrast distinction in MR imaging, wherein the clear contrast distinction is bright vs dark in two different phases of the composition after administration into the human or animal body, and wherein the bright or dark phase is provided by said non-water soluble carbohydrates, wherein the disaccharides have structures selected from:

Formulae:

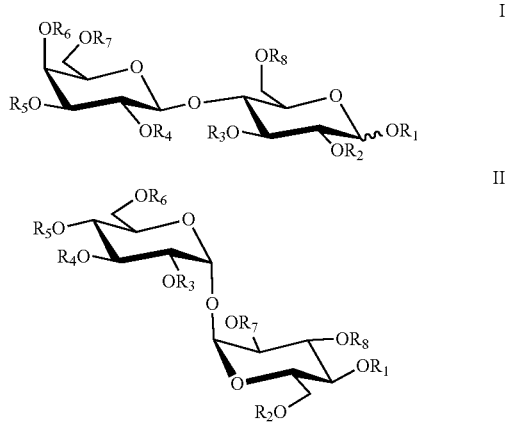

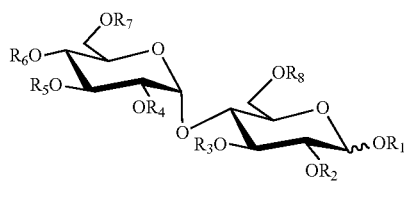

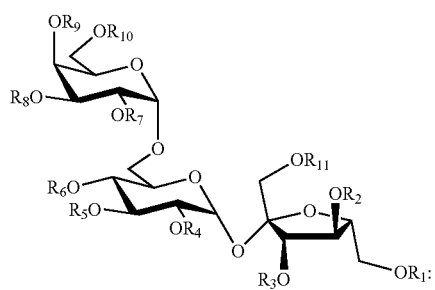

wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and further comprising pure anomers or mixtures of α- and β-anomers of structural Formulae of I, II, III, wherein the composition contains an MR imaging contrast agent containing at least one of gadolinium associated with a chelate chosen from PLA-DTPA or PLA-DOTA polymer chelates, or gadolinium-chelating lipids with DOPE-DOTA(Gd) or BSA-DTPA.

2. The composition for at least MR imaging according to claim 1, wherein the composition is for combined MR and CT imaging, and wherein the composition provides a clear distinction between CT contrast and MRI contrast in a marker.

3. The composition for at least MR imaging according to claim 1, wherein the composition is a liquid before administration into the human or animal body that increases in viscosity by more than 10,000 centipoise (cP) after administration into the human or animal body.

4. The composition for at least MR imaging according to claim 1, wherein the composition is a liquid before administration and transforms into a gel-like material after administration.

5. The composition for at least MR imaging according to claim 1, wherein the composition becomes a solid material after administration, selected from a crystalline or amorphous solid.

6. The composition for at least MR imaging according to claim 1, wherein an increase in viscosity after administration into the human or animal body is due to diffusion of a solvent-like molecule out of the administered material and into surrounding tissue.

7. The composition for at least MR imaging according to claim 1, wherein the non-water soluble carbohydrates are trisaccharides with structures selected from:

wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and further comprising pure anomers or mixtures of α- and β-anomers of structural Formulae of IV.

8. The composition for at least MR imaging according to claim 1,
wherein at least 50% of the non-water soluble carbohydrates are mono- or
oligosaccharides containing at least one amino sugar unit.

9. The composition for at least MR imaging according to claim 8, wherein the amino sugar has the structure:

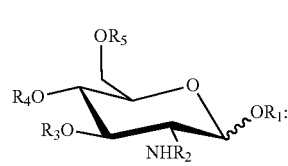

wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, and mono-, di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and further comprising pure anomers or mixtures of anomers of α- and β- anomers centres of structural Formulae of V.

10. The composition according to claim 1, wherein the non-water soluble carbohydrates comprises poly(ethylene glycol-b-caprolactone) (PEG-PCl), sucrose acetate isobutyrate (SAIB), poly(D,L-lactic acid), or poly(lactic-co-glycolic acid) (PGLA), or a combination thereof.

11. The composition for at least MR imaging according to claim 1, wherein the non-water soluble carbohydrates comprise mixed saccharides of furanose and pyranose.

12. The composition for at least MR imaging according to claim 1, wherein said at least one imaging contrast agent makes the composition visible by PET imaging, SPECT imaging, Ultrasound imaging, CT imaging, MR imaging, x-ray imaging, fluoroscopy imaging, fluorescence imaging, or OCT imaging.

13. The composition for at least MR imaging according to claim 1, wherein the composition contains two imaging contrast agents that are visible by at least two imaging methods, chosen from PET imaging, SPECT imaging, Ultrasound imaging, CT imaging, MR imaging, x-ray imaging, fluoroscopy imaging, fluorescence imaging, or OCT imaging.

14. The composition for at least MR imaging according to claim 1, wherein the composition contains an imaging contrast agent for CT imaging and an imaging contrast agent for MR imaging.

15. The composition for at least MR imaging according to claim 1, wherein the composition contains an MR imaging contrast agent containing gadolinium associated with a chelate.

16. The composition for at least MR imaging according to claim 1, wherein the composition contains an MR imaging contrast agent containing gadolinium associated with a chelate that is covalent linked to a polymer.

17. The composition for at least MR imaging according to claim 1, wherein the composition contains an MR imaging contrast agent containing gadolinium associated with a chelate that is covalent linked to poly lactic acid (PLA).

18. The composition for at least MR imaging according to claim 1, wherein the composition contains a CT contrast agent and an MR imaging contrast agent containing Gadolinium associated with a chelate, and wherein the CT contrast agent is hydrophobic.

19. The composition for at least MR imaging according to claim 1, wherein the composition comprises a pharmacologically active compound that is released into surrounding tissue.

\* \* \* \* \*